United States Patent
Hansen et al.

(10) Patent No.: US 12,303,335 B2
(45) Date of Patent: May 20, 2025

(54) SYSTEMS AND METHODS FOR CONTROLLING VISUALIZATION OF ULTRASOUND IMAGE DATA

(71) Applicant: Clarius Mobile Health Corp., Burnaby (CA)

(72) Inventors: Trevor Stephen Hansen, Vancouver (CA); Benjamin Eric Kerby, Richmond (CA)

(73) Assignee: Clarius Mobile Health Corp., Vancouver (CA)

( * ) Notice: Subject to any disclaimer, the term of this patent is extended or adjusted under 35 U.S.C. 154(b) by 191 days.

(21) Appl. No.: 16/927,876

(22) Filed: Jul. 13, 2020

(65) Prior Publication Data
US 2020/0337678 A1 Oct. 29, 2020

Related U.S. Application Data

(63) Continuation of application No. 15/336,775, filed on Oct. 27, 2016, now Pat. No. 10,709,422.

(51) Int. Cl.
*A61B 8/00* (2006.01)

(52) U.S. Cl.
CPC .............. *A61B 8/467* (2013.01); *A61B 8/465* (2013.01); *A61B 8/469* (2013.01); *A61B 8/54* (2013.01)

(58) Field of Classification Search
CPC ......... A61B 8/467; A61B 8/465; A61B 8/469; A61B 8/54
See application file for complete search history.

(56) References Cited

U.S. PATENT DOCUMENTS

| 6,061,059 A | 5/2000 | Taylor et al. |
| 6,251,073 B1 | 6/2001 | Imran et al. |
| (Continued) | | |

FOREIGN PATENT DOCUMENTS

| EP | 2254033 A1 | 11/2010 |

OTHER PUBLICATIONS https://web.archive.org/web/20130106181843/http://www.word-2010.com/word-save-as-pdf (Year: 2012).*

(Continued)

*Primary Examiner* — John D Li
(74) *Attorney, Agent, or Firm* — Julian Ho; Susan Ben-Oliel

(57) ABSTRACT

The present embodiments relate generally to systems and methods for controlling visualization of ultrasound image data. The systems can be configured to display a live ultrasound image feed on a touchscreen and receive input via the touchscreen to adjust imaging parameters of the live ultrasound image feed, with the input having continuous contact with the touchscreen. During the continuous contact with the touchscreen, a transitional view of the live ultrasound image feed can be displayed, with the transitional view being continuously updated to indicate previews of the live ultrasound image feed with the imaging parameters adjusted. The continuous updating can be performed in accordance with characteristics of the contact with the touchscreen and while the transitional view continues the display of the live ultrasound image feed. Upon termination of the continuous contact with the touchscreen, a selected setting of the imaging parameters being adjusted can be identified, with the selected setting being identified based on the preview that is displayed when the continuous contact with the touchscreen is terminated.

20 Claims, 12 Drawing Sheets

(56) References Cited

U.S. PATENT DOCUMENTS

| | | |
|---|---|---|
| 6,569,102 B2 | 5/2003 | Imran et al. |
| 7,022,075 B2 | 4/2006 | Grunwald et al. |
| 8,884,888 B2 | 11/2014 | Chin |
| 2002/0173721 A1 | 11/2002 | Grunwald et al. |
| 2003/0013959 A1 | 1/2003 | Grunwald et al. |
| 2003/0158405 A1 | 8/2003 | McKew et al. |
| 2004/0138569 A1* | 7/2004 | Grunwald ............. G16H 40/63 600/459 |
| 2006/0111634 A1 | 5/2006 | Wu |
| 2006/0116578 A1 | 6/2006 | Grunwald et al. |
| 2008/0218588 A1* | 9/2008 | Stetten .................. A61B 8/462 348/46 |
| 2009/0043195 A1* | 2/2009 | Poland .................. A61B 8/461 600/437 |
| 2010/0298701 A1 | 11/2010 | Shin |
| 2011/0137156 A1* | 6/2011 | Razzaque .......... A61B 18/1477 600/424 |
| 2013/0232409 A1* | 9/2013 | Cranfill ................ G06F 3/0488 715/256 |
| 2013/0254705 A1 | 9/2013 | Mooring et al. |
| 2013/0275077 A1 | 10/2013 | Kim et al. |
| 2014/0098049 A1 | 4/2014 | Koch et al. |
| 2014/0114190 A1 | 4/2014 | Chiang et al. |
| 2014/0121524 A1 | 5/2014 | Chiang et al. |

OTHER PUBLICATIONS

GE Healthcare, "Vscan with Dual Probe Knobology", video uploaded May 5, 2015 by GE Healthcare, available at https://www.youtube.com/watch?v=w0kGskj6WAs, last accessed Dec. 13, 2016.

Info Healcerion, "Sonon 300C Instruction (English version)", video published Jan. 19, 2016 by Info Healcerion, available at https://www.youtube.com/watch?v=V4DZqPKyMcM, last accessed Dec. 13, 2016.

Keebomed Inc, "Chison SonoTouch 30 | Portable Touchscreen Ultrasound", video published Oct. 29, 2014 by Keebomed Inc, available at https://www.youtube.com/watch?v=39hMvvG0n8M, last accessed Dec. 13, 2016.

United Medical Instruments, Inc., "uSmart 3200T Ultrasound Smart Gestures", video published May 15, 2014 by United Medical Instruments, Inc., available at https://www.youtube.com/watch?v=3Lqkc6mlwvw, last accessed Dec. 13, 2016.

Chris Moore, "Current Issues with Emergency Cardiac Ultrasound Probe and Image Conventions", Academic Emergency Medicine, 2008, 15 (3), 278-284.

Craig Villamor, Dan Willis, and Luke Wroblewski, "Touch Gestures Reference Guide", last updated Apr. 15, 2010, available at http://www.lukew.com/touch/, last accessed Dec. 13, 2016.

* cited by examiner

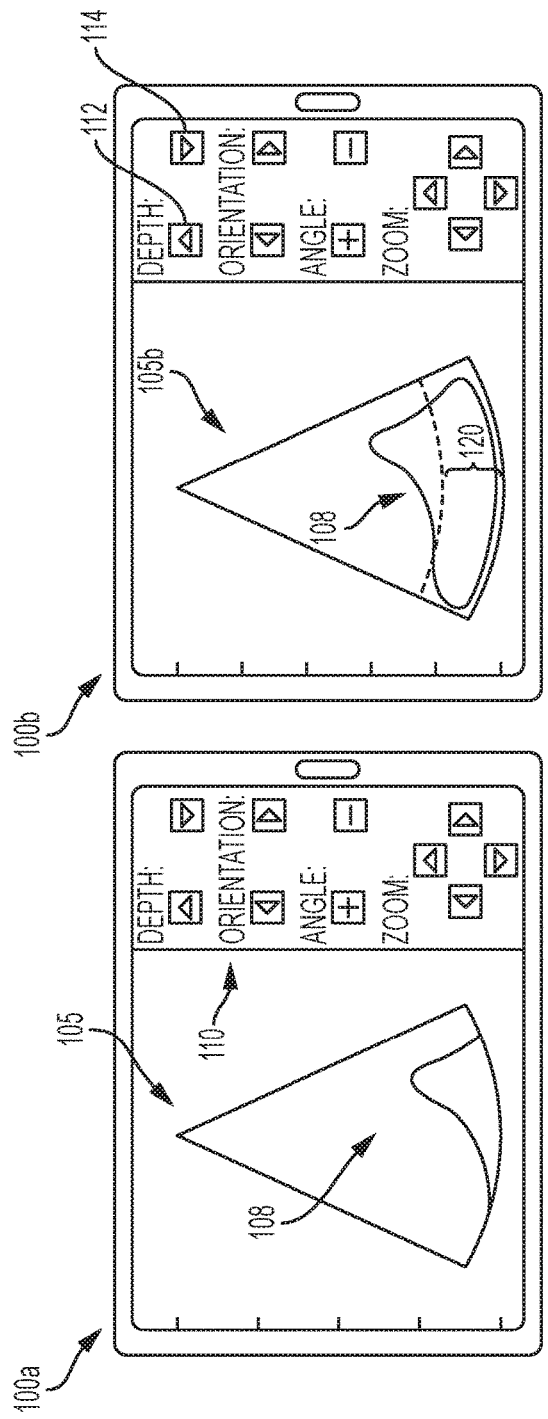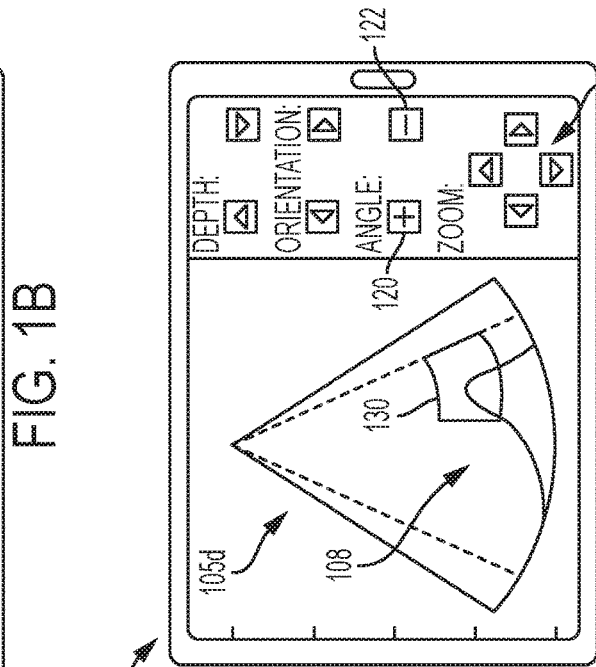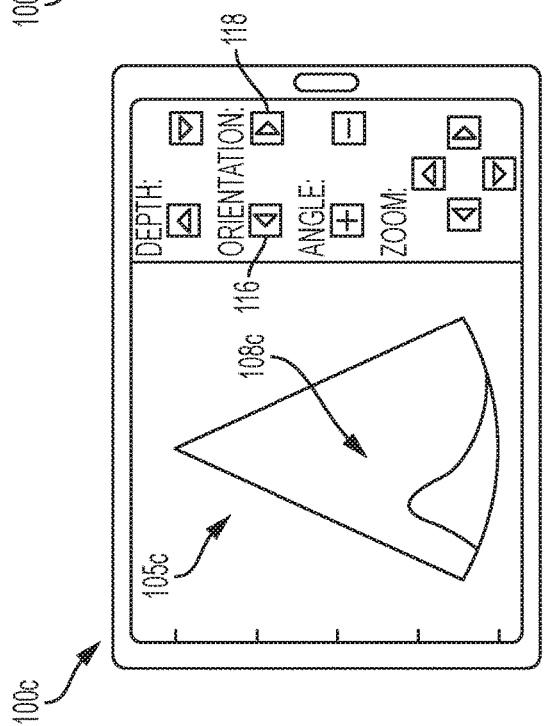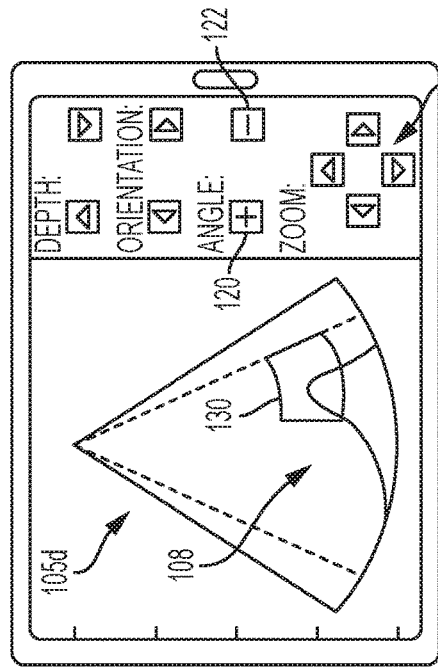

SYSTEMS AND METHODS FOR CONTROLLING VISUALIZATION OF ULTRASOUND IMAGE DATA

CROSS-REFERENCE TO RELATED APPLICATION

This application is a continuation of U.S. patent application Ser. No. 15/336,775 entitled "SYSTEMS AND METHODS FOR CONTROLLING VISUALIZATION OF ULTRASOUND IMAGE DATA" filed Oct. 27, 2016. The entire contents of U.S. patent application Ser. No. 15/336,775 are hereby incorporated by reference.

FIELD

The present disclosure relates generally to ultrasound imaging, and in particular, to systems and methods for controlling visualization of ultrasound image data.

BACKGROUND

Ultrasound imaging systems are a powerful tool for performing real-time, non-invasive imaging procedures in a wide range of medical applications. An ultrasound machine includes a transducer which sends out ultrasound signals into the tissue. Ultrasound waves are reflected back from the tissue and are received by the ultrasound machine. The reflected signals are processed to produce an ultrasound image of the target anatomy. The ultrasound machine has a user input device by which the operator of the ultrasound machine can control the machine to obtain images of tissue structures. Traditionally, the images may be displayed on a display incorporated in the ultrasound machine, and the user input device may include a keyboard.

A challenging part of acquiring ultrasound images is adjusting the various imaging parameters to locate and view the target anatomy. For example, ultrasound operators may typically attempt to focus target tissue in the center and so that it fills the screen. Conventional ultrasound systems have large physical control interfaces with numerous controls which allow operators to adjust a wide range of parameters. The controls may not be intuitive to operate, and users may require extensive training to learn the location and operation of these controls.

There is an increasing demand for small portable ultrasound imaging devices that are easier to operate and that acquire good quality ultrasound images of the target anatomy. Increasing portability and simplicity often involves or requires reducing the number of controls to accommodate smaller screens and smaller devices. Conventional ultrasound machines that include keyboards can be bulky and thus less portable.

Even on some existing ultrasound systems that provide ultrasound images on a touchscreen display, on-screen controls may not provide a way to adjust imaging parameters in a manner that easily allows the imaging parameters to be previewed prior to adjustment.

There is thus a need for improved systems and methods for controlling visualization of ultrasound image data. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which:

FIGS. 1A-1D shows example traditional methods of controlling visualization of ultrasound image data;

DETAILED DESCRIPTION

Figure 2:
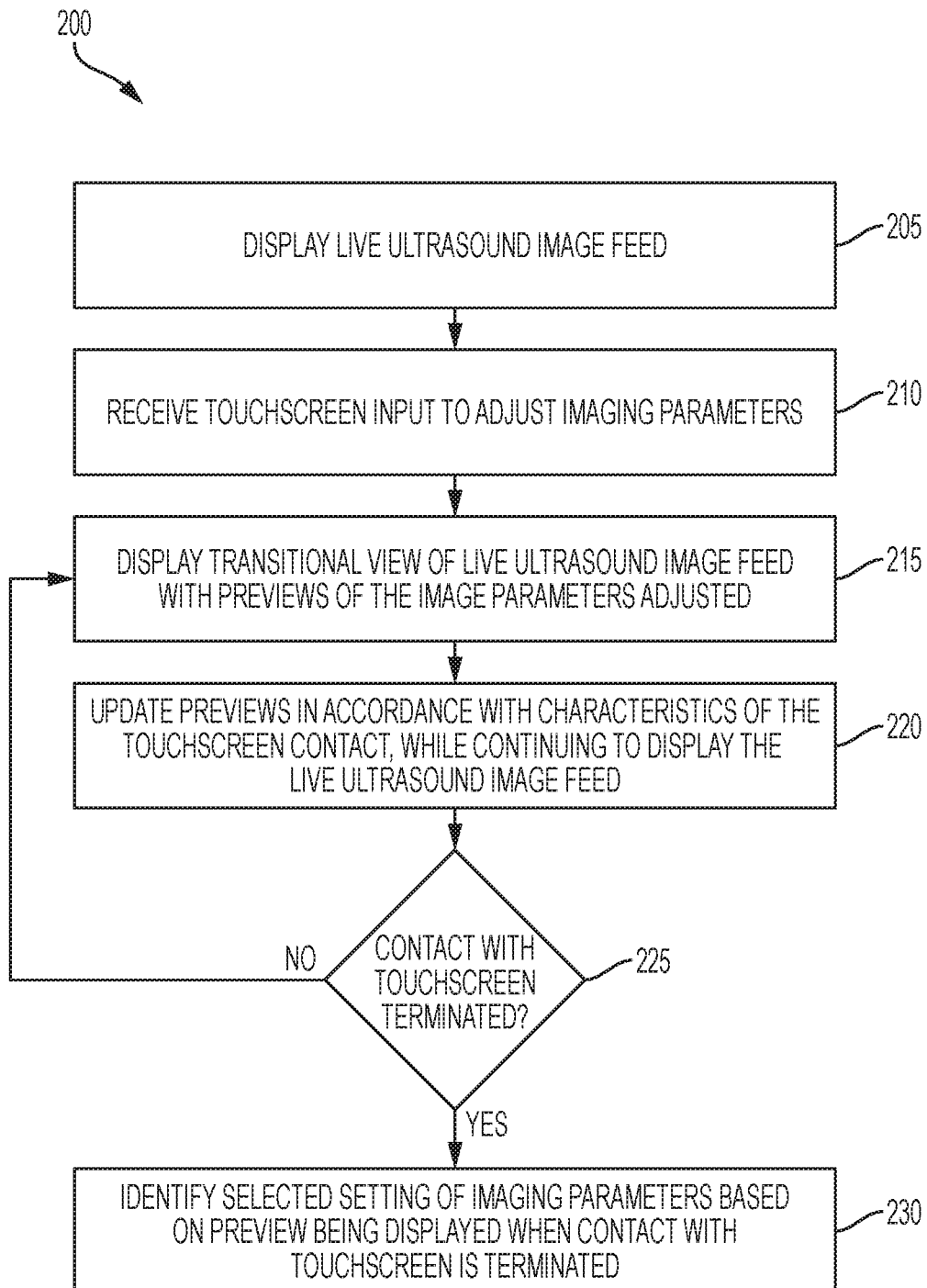
FIG. 2 is a flowchart diagram for steps of a method of controlling visualization of ultrasound image data, in accordance with at least one embodiment of the present invention.

In a first broad aspect of the present disclosure, there is provided a method of controlling visualization of ultrasound image data. The method may include: displaying a live ultrasound image feed on a touchscreen; receiving input via the touchscreen to adjust imaging parameters of the live ultrasound image feed, the input having continuous contact with the touchscreen; during the continuous contact with the touchscreen, displaying a transitional view of the live ultrasound image feed, the transitional view being continuously updated to indicate previews of the live ultrasound image feed with the imaging parameters adjusted, the continuous updating being performed in accordance with characteristics of the contact with the touchscreen and while the transitional view continues the display of the live ultrasound image feed; and upon termination of the continuous contact with the touchscreen, identifying a selected setting of the imaging parameters being adjusted, the selected setting being identified based on the preview that is displayed when the continuous contact with the touchscreen is terminated.

In some embodiments, the live ultrasound image feed is generated from an ultrasound acquisition unit configured to transmit and receive ultrasound signals, and scan conversion is repeatedly performed on image data corresponding to the ultrasound signals, to configure the image data for displaying the previews of the live ultrasound image feed. In some embodiments, the ultrasound signals are transmitted and received according to an ultrasound sequence, and the repeated scan conversion is performed on the image data corresponding to the ultrasound signals, without altering the ultrasound sequence.

In some embodiments, the method involves transmitting the selected setting to an ultrasound acquisition unit to cause the ultrasound acquisition unit to modify the live ultrasound image feed, so that the live ultrasound image feed has adjusted imaging parameters that reflect the selected setting.

In some embodiments, the ultrasound acquisition unit is configured to transmit and receive ultrasound signals according to an ultrasound sequence when generating the live ultrasound image feed, and the selected setting is used to alter the ultrasound sequence when modifying the live ultrasound image feed.

In some embodiments, the imaging parameters include an imaging depth of the live ultrasound image feed, and the previews of the live ultrasound image feed correspond to an adjustable scale showing selectable imaging depths. In some embodiments, the selected setting includes one of the selectable imaging depths shown on the adjustable scale. In some embodiments, the continuous contact with the touchscreen corresponds to a drag gesture, and the adjustable scale is continuously updated to show the selectable imaging depths in correspondence with a length of the drag gesture. In some embodiments, the imaging depths displayed in the previews of the live ultrasound image feed correspond to the adjustable scale that is being continuously updated.

In some embodiments, the input to adjust the imaging parameters includes input for flipping the live ultrasound image feed along one of a vertical or a horizontal axis. In some embodiments, the continuous contact with the touchscreen corresponds to a drag gesture, and the previews of the live ultrasound image feed include an animation from a pre-flipped orientation of the live ultrasound image feed to a flipped orientation of the live ultrasound image feed. In some embodiments, the transitional view being continuously updated to correspond to characteristics of the contact with the touchscreen includes the animation being continuously updated to correspond with a length of the drag gesture.

In some embodiments, the live ultrasound image feed includes a sector image, and the input to adjust the imaging parameters includes input for altering a sector angle of the sector image. In some embodiments, the continuous contact with the touchscreen corresponds to a pinch gesture, and the previews of the live ultrasound image feed decrease the sector angle upon a pinch-in gesture and increase the sector angle upon a pinch-out gesture.

In some embodiments, the input to adjust the imaging parameters includes input for creating a region of interest (ROI) box for use in a write zoom operation on the live ultrasound image feed. In some embodiments, the continuous contact with the touchscreen corresponds to a pinch gesture, and the previews of the live ultrasound image feed include performing read zoom operations on the live ultrasound image feed.

In another broad aspect of the present disclosure, there is provided an ultrasound imaging system including: an ultrasound acquisition unit configured to transmit and receive ultrasound signals; and a display unit having a touchscreen, the display unit being communicably coupled to the ultrasound acquisition unit. The display unit can be configured to: display a live ultrasound image feed on the touchscreen; receive input via the touchscreen to adjust imaging parameters of the live ultrasound image feed, the input including continuous contact with the touchscreen; during the continuous contact with the touchscreen, display a transitional view of the live ultrasound image feed, the transitional view being continuously updated to indicate previews of the live ultrasound image feed with the imaging parameters adjusted, the continuous updating being performed in accordance with characteristics of the contact with the touchscreen and while the transitional view continues the display of the live ultrasound image feed; and upon termination of the continuous contact with the touchscreen, identify a selected setting of the imaging parameters being adjusted, the selected setting being identified based on the preview that is displayed when the continuous contact with the touchscreen is terminated.

In some embodiments, the live ultrasound image feed is generated from image data corresponding to the ultrasound signals, and scan conversion is repeatedly performed on the image data to configure the image data for displaying the previews of the live ultrasound image feed. In some embodiments, the ultrasound signals are transmitted and received according to an ultrasound sequence, and the repeated scan conversion is performed on the image data corresponding to the ultrasound signals, without altering the ultrasound sequence.

In some embodiments, the ultrasound acquisition unit is configured to transmit and receive the ultrasound signals according to an ultrasound sequence when generating the live ultrasound image feed, and the selected setting is used to alter the ultrasound sequence.

In another broad aspect of the present disclosure, there is provided a computer readable medium storing instructions for execution by a processor of a display unit having a touchscreen, wherein when the instructions are executed by the processor, the display unit is configured to: display a live ultrasound image feed on the touchscreen; receive input via the touchscreen to adjust imaging parameters of the live ultrasound image feed, the input including continuous contact with the touchscreen; during the continuous contact with the touchscreen, display a transitional view of the live ultrasound image feed, the transitional view being continuously updated to indicate previews of the live ultrasound image feed with the imaging parameters adjusted, the continuous updating being performed in accordance with characteristics of the contact with the touchscreen and while the transitional view continues the display of the live ultrasound image feed; and upon termination of the continuous contact with the touchscreen, identify a selected setting of the imaging parameters being adjusted, the selected setting being identified based on the preview that is displayed when the continuous contact with the touchscreen is terminated.

In some embodiments, the method may involve transmitting a communication to an ultrasound probe, where such communication is to increase the imaging depth if a vertical component of a detected drag gesture is in a direction away from the skin line and where such communication is to decrease the imaging depth if a vertical component of the drag gesture is in a direction toward the skin line.

In some embodiments, the acquired ultrasound images are displayed on an electronic display unit in real time while the transitional view and associated previews are being displayed. In some embodiments, the ultrasound image feed is frozen/paused while the transitional view and associated previews are being displayed, and resumed after a setting for the imaging parameter being previewed is selected.

In some embodiments, input may be a touch gesture to rotate the image. In some embodiments, the degree of rotation may depend on the distance a visual orientation indicator is from the center of the display.

In some embodiments, an electronic display unit interprets the drag gesture to adjust either the pan or imaging depth based on the zoom state of the displayed image.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIGS. 1A-1D, shown there generally as 100a-100d are a number example traditional user interfaces which allow for modification of imaging parameters. As discussed above, conventional ultrasound imaging systems may be provided with a keyboard or other physical control for inputting a number of different imaging parameters during ultrasound imaging. Some example imaging parameters that may be controlled in this manner are the imaging depth of an ultrasound image feed, the orientation of the ultrasound image feed, a sector angle of a sector ultrasound image feed, and/or the placement of a region of interest (ROI) location for performing a high-definition (HD) zoom (also called a write zoom).

While some more recent ultrasound imaging systems may incorporate touchscreen displays for receiving input to modify imaging parameters, the user interfaces provided by these systems typically mimic the operation of the physical buttons available on traditional ultrasound systems. For example, these types of systems may provide virtual buttons and controls that can be pressed to input imaging parameters.

Referring to FIG. 1A, shown there generally as 100a is an example of such an ultrasound user interface on a touchscreen display. As shown, it can be seen that while an ultrasound image feed 105 (showing structure 108) is viewable, some attempts at allowing control of imaging parameters on a touchscreen interface may mimic physical controls by providing virtual on-screen buttons 110 that receive input of imaging parameters. For example, as shown, there may be depth control buttons that allow modification of the imaging depth of an ultrasound image feed; orientation buttons that alter the rotational orientation of an ultrasound image feed; angle buttons that allow for increase or decrease of a sector ultrasound image feed, and/or a multi-directional set of buttons for positioning a ROI for performing a HD zoom operation. FIGS. 1B-1D each illustrate how the ultrasound image feed 105 of FIG. 1A may be updated in three different scenarios, when these traditional controls are used.

Referring to FIG. 1B, shown there generally as 100b is an example of how the depth controls 112, 114 may be used to update the image feed. For example, when the depth control buttons 112, 114 are used to increase the imaging depth, it can be seen that the ultrasound image 105b is updated to show an increase 120 in imaging depth. As illustrated, the previous imaging depth of the image feed 105 of FIG. 1A is shown in dotted outline once the depth is increased, and the scale for the imaging depth on the left of the display has been updated. As a result, it can be seen that more of the structure 108 (which was only partially viewable in FIG. 1A) is viewable in FIG. 1B.

A challenge that arises with the use of physical or virtual buttons to adjust imaging depth is that they are usually provided in a configuration where there is an 'up' button 112 and a 'down' button 114, which do not clearly indicate how the pressing of either button alters the imaging depth. For example, some users may interpret the pressing of an 'up' button 112 as signaling a shifting 'up' of the imaging depth (e.g., a decrease in the imaging depth). However, certain other users may interpret the pressing of an 'up' button 112 as increasing the imaging depth. Correspondingly, some users may interpret the pressing of a 'down' button 114 as signalling a shifting 'down' of the imaging depth (e.g., an increase in the imaging depth); while certain other users may interpret the pressing of a 'down' button 114 as decreasing the imaging depth. Thus, the pressing of the traditional 'up' and 'down buttons 112, 114 to adjust imaging depth may cause confusion for users. To the extent a press of either button 112, 114 causes an unexpected result for the user, they may typically have to press the other button twice (once to restore the original depth, and again to actually adjust the imaging depth in the desired direction). This may cause inconvenience and delays for ultrasound operators. As discussed below in the context of FIGS. 3A-3C and 4A-4C, the present embodiments may address some of these shortcomings.

Referring to FIG. 1C, shown there generally as 100c is an example of how the orientation controls can be used to rotate an ultrasound image. For example, the buttons 116, 118 may be used to rotate the ultrasound image along a vertical axis (e.g., to flip the ultrasound image along a vertical axis intersecting through the center of the ultrasound image 105c). As illustrated, upon pressing buttons of such an orientation control, the ultrasound image previously shown in FIG. 1A may be shown as being flipped, so that the structure 108c viewable in FIG. 1A is flipped (e.g., the protrusion in the structure 108 appearing on the right side of the ultrasound image feed 105 in FIG. 1A now appears on the left side of the ultrasound image feed 105c in FIG. 1C).

Referring to FIG. 1D, shown there generally as 100d is an example of how the sector angle controls on a traditional touchscreen user interface may be provided. For example, as illustrated, when the '+' button 120 is pressed, the sector angle of the sector image feed 105 previously shown in FIG. 1A may be increased to the angle shown in the sector image 105d of FIG. 1D (the original sector angle of FIG. 1A is shown in dotted outline in FIG. 1D). Correspondingly, a '−' button 122 may also be pressed to decrease the sector angle. As illustrated, the structure 108 remains viewable in the sector ultrasound image feed 105d of FIG. 1D.

FIG. 1D also illustrates how a ROI box may be moved when locating it on an ultrasound image 105d for the purpose of performing a HD zoom. As will be understood by persons skilled in the art, there may be different types of zoom operations that can be performed on an ultrasound image feed to allow review of portions of an ultrasound image feed in greater detail. For example, a read zoom operation may allow magnification of a part of the image that already exists on the display. In this type of operation, the image data already stored in memory is read to display the selected ROI, and the zoomed-in area may be moved to examine different parts of the image. However, since read zoom operations rely on the original image data, there may be fewer lines of lateral resolution in the appearance of the zoomed-in area. In contrast, when performing a write zoom operation, the ROI box 130 is first positioned for the purpose of identifying a region on which the ultrasound and echo signals should be targeted. Then, scanning is limited to the identified area with a higher number of more closely spaced ultrasound signals. As compared to performing a read zoom, this allows for improved image quality (e.g., increased frame rate and/or improved lateral resolution) in the resultant zoomed-in image.

In traditional ultrasound user interfaces, the location of the ROI box 130 may be adjusted using a track ball to position the ROI box 130 over the image area that is desired to be examined in greater detail. As illustrated in FIG. 1D, even in some touchscreen ultrasound user interfaces, a similar set of directional controls 126 may be provided to move the ROI box 130 in various directions.

However, positioning the ROI box 130 in this manner may be inefficient because prior to each button press, the user does not have any indication of where the ROI box 130 may be positioned after the button has been pressed (e.g., there is no indication how much each button press may move the ROI box 130 in a given direction). As a result, the ultrasound operator may have to position the ROI box 130 via trial and error, and repeatedly press various buttons to position the ROI box 130 in the desired location.

Indeed, this is a common challenge amongst the different types of user interface controls discussed in FIGS. 1A-1D (e.g., depth, orientation, and sector angle). For example, in the example of the image depth shown in FIG. 1B, a button press of buttons 112, 114 may not necessarily indicate the amount the image depth will increase or decrease until after a button is pressed. Similarly, for the orientation change shown in FIG. 1C, a button press of orientation buttons 116, 118 may not necessarily indicate whether a button press will confirm a given orientation already shown or further rotate the ultrasound image. Moreover, for the sector angle increase and decrease controls 120, 122, a press of a button may not indicate how the sector angle of the sector image 105*d* will change until after the buttons 120, 122 are pressed. As discussed in greater detail below, the embodiments described herein may help to alleviate some of these drawbacks.

Referring to FIG. 2, shown there generally as 200 is a flowchart diagram for acts of a method of controlling visualization of ultrasound image data, in accordance with at least one embodiment of the present invention. In some embodiments, the various acts shown in FIG. 2 may be performed by the ultrasound machine shown in FIG. 10. In various embodiments, the method of FIG. 2 may be performed in the context of the adjustment of any ultrasound imaging parameters. However, for the purpose of illustration, FIG. 2 will be discussed in the context of adjusting the following example imaging parameters and with reference to the noted figures: imaging depth (FIGS. 3A-3C, 4A-4C); orientation (FIGS. 5A-5D, 6); HD zoom (FIGS. 7A-7C); and sector angle (FIGS. 8A-8C, 9A-9C). In particular, the discussion immediately below will be made with reference to FIGS. 3A-3C. However, subsequent discussion of the following figures will also be made with reference to the method of FIG. 2.

Figure 3A:
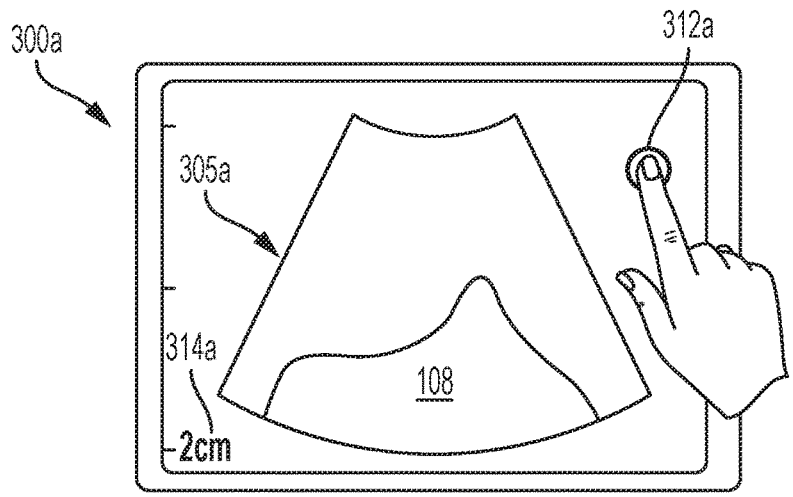
FIGS. 3A-3C are a sequence of user interface interactions for receiving input to increase the depth imaging parameter during ultrasound imaging, in accordance with at least one embodiment of the present invention.

At 205, the method involves displaying a live ultrasound image feed on a touchscreen. For example, ultrasound signal data may be generated from scanning tissue and the resultant live image feed being displayed on a touchscreen interface such as is shown in FIG. 3A.

At 210, input may be received via the touchscreen to adjust imaging parameters of the live ultrasound image feed. For example, the input may include continuous contact with the touchscreen. Referring simultaneously to FIG. 3A, shown there generally as 300*a* is an ultrasound image feed 305*a* showing structure 108. As shown in FIG. 3A, there is also an imaging depth indicator 314*a* showing that the imaging depth of the ultrasound image feed 305*a* is '2 cm'. As will be understood by persons skilled in the art, ultrasound waves penetrate tissue at varying depths based on the frequency of the ultrasound waves emitted. For example, lower frequencies may be used to penetrate further into the tissue (at the cost of decreased axial resolution in the ultrasound image). Additionally, the ultrasound signal beams can be focused at different depths. In some embodiments, modification of the image depth may involve modification of different ultrasound parameters such as the frequency of the ultrasound signals and/or the focal depths. The image depth imaging parameter may be adjusted by touchscreen input that requires continuous contact with the touchscreen. For example, as illustrated in FIG. 3A, such input may be initiated when a touch is received at 312*a*.

Figure 3B:
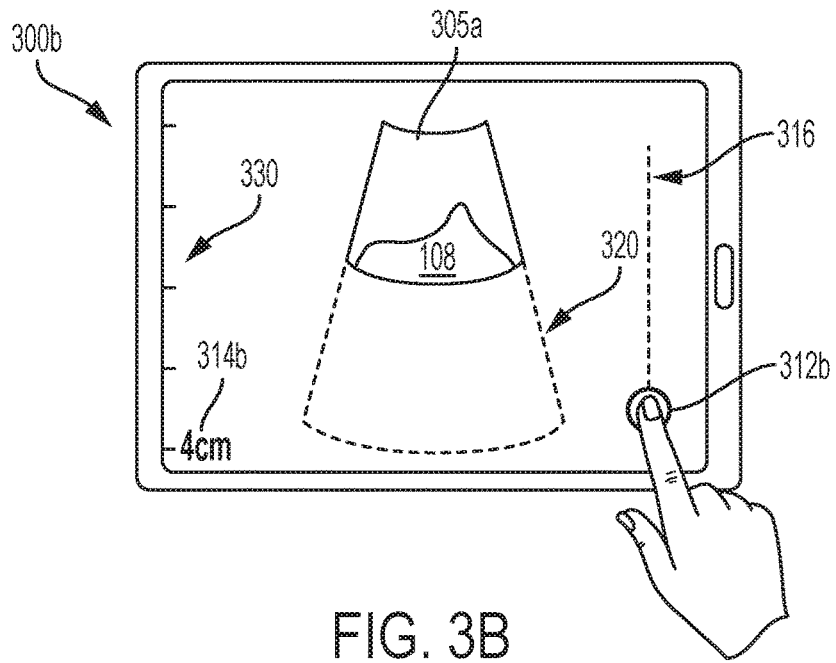

Referring back to FIG. 2, at 215, a transitional view of the live ultrasound image feed may be displayed with previews of the image parameters adjusted. In some embodiments, the transitional view is displayed during continuous contact with the touchscreen. Referring simultaneously to FIG. 3B, show there generally as 300*b* is an example transitional view of the ultrasound image feed 305*a* when adjusting imaging depth, in accordance with an embodiment of the present invention. FIG. 3B illustrates an example user interface interaction at a point in time after contact with the touchscreen is initiated in FIG. 3A. As illustrated, a drag gesture is initiated in FIG. 3A, and continuous contact with the touchscreen is maintained through the touch path 316 (shown in dotted outline) to touch point 312*b*. In response, the touchscreen may display a transitional view during the continuous contact that provides previews 320 of the image depth being adjusted. In various user interface sequences shown herein, circles are shown for touch points and dotted lines are shown for touch paths where a user maintains touch with the touchscreen during a touch gesture (e.g., a drag or pinch gesture). However, these circles and dotted lines are only provided in the figures of the present disclosure to illustrate the touch points and/or touch path of a touch gesture, and may not be actually outputted on the display in a viewable manner.

Referring back to FIG. 2, at act 220, the previews 320 may be updated in accordance with characteristics of the contact with the touchscreen and while the transitional view continues the display of the live ultrasound image feed. Referring again to FIG. 3B, the illustrated example embodiment may update the appearance of the ultrasound image feed to show a preview 320 of the image depth that corresponds to characteristics of the touch on the touchscreen. For example, the previews 320 of the live ultrasound image feed 305*a* may correspond to an adjustable scale 330 showing selectable imaging depths, which continuously updates in correspondence with a length of the drag gesture. In some embodiments, the imaging depths displayed in the previews 320 of the live ultrasound image feed 305a correspond to the adjustable scale that is being continuously updated. For example, as shown, the adjustable scale 330 may increase as the length of the drag gesture initiated in FIG. 3A increases, so that after the drag gesture has been progressed through the touch path 316, the image depth indicator 314b and corresponding preview of the image depth of the live ultrasound image feed is updated to show '4 cm'.

In some embodiments, as the adjustable scale 330 showing selectable image depths is being continuously updated, the live ultrasound image feed originally appearing prior to the beginning of the contact with the touchscreen (e.g., image feed 305a from FIG. 3A in the illustrated examples) may continue to be displayed in real time. For example, as the previews 320 show what the projected image depth is expected to be based on the characteristics of the touch (as shown in dotted outline in FIG. 3B), image data from the ultrasound image feed 305a originally viewable in FIG. 3A can remain viewable in the transitional view. However, since the original ultrasound image feed 305a is only imaging to a shallower image depth of '2 cm', the appearance of the ultrasound image feed 305a is adjusted in the preview 320 to show how image data from the original ultrasound image feed 305a would appear after selection of the imaging depth that is being shown (e.g., '4 cm').

In various embodiments, the live ultrasound image feed 305a viewable prior to the touch being initiated may be generated from an ultrasound acquisition unit configured to transmit and receive ultrasound signals (e.g., ultrasound acquisition unit 1004 in FIG. 10, discussed below). When generating the transitional view encompassing the previews 320 and the modified version of the original ultrasound image feed 305a, scan conversion may be repeatedly performed on the image data from the ultrasound signals to configure such data for displaying the previews of the live ultrasound image feed 305a. For example, in the example embodiments illustrated in FIGS. 3A-3B, scan conversion may need to be repeatedly performed to adapt the image data being acquired: from being displayed on the entirety of the touchscreen in FIG. 3A to only a smaller portion of the touchscreen reflective of the previewed image depth in FIG. 3B.

As will be understood by persons skilled in the art, the ultrasound acquisition unit may be configured to transmit and receive ultrasound signals according to an ultrasound sequence when generating the live ultrasound image feed 305a (e.g., the sequence and characteristics in which ultrasound pulses are directed to the tissue and the resultant echo signals received). In some embodiments, the imaging parameters being adjusted may require the ultrasound sequence being used by the ultrasound acquisition unit to be altered. For example, when altering imaging depth, the frequency and/or focus of the ultrasound pulses directed from the ultrasound acquisition unit may need to be changed if the desired imaging depth is deeper or shallower.

When generating the transitional view, in some embodiments, the noted scan conversion may be repeatedly performed without altering the ultrasound sequence. Since reloading the ultrasound sequence requires some time (e.g., approximately 100 milliseconds), frequently uploading the ultrasound sequence may cause the display of the ultrasound image feed to flicker or jerk after each ultrasound sequence is reloaded. By configuring the ultrasound sequence to remain unaltered throughout the transitional view showing the previews 320, the same original ultrasound image feed 305a can remain viewable without any jumps, flicker or other visual interruption. Scan conversion and the modification of ultrasound sequences are discussed in greater detail below with respect to FIG. 10.

Referring back to FIG. 2, at step 225, it may be determined whether contact with the touchscreen has terminated. If contact with the touchscreen has not terminated (the 'NO' branch at act 225), the method may proceed back to act 215 and continue to display the transitional view of the imaging parameter being adjusted. If it is determined that contact with touchscreen has terminated (the 'YES' branch at act 225), the method may proceed to act 230. For example, in some embodiments, this determination may be made upon termination of a drag gesture or other touch-based gesture.

At 230, upon termination of the continuous contact with the touchscreen, the method may involve identifying a selected setting from the imaging parameter being adjusted, with the selected setting being identified based on the preview that is displayed when the continuous contact with the touchscreen is terminated. For example, in the context of the example scenario discussed with reference to FIG. 3B, upon termination of the drag gesture shown in FIG. 3B, the imaging depth being shown in the adjustable scale 330 and/or the preview 320 may be identified as the selected setting for the imaging depth. If the contact with the touchscreen is released at the point shown in FIG. 3B, the imaging depth of '4 cm' shown on the imaging depth indicator 314b may be selected as the imaging depth that is desired.

Figure 3C:
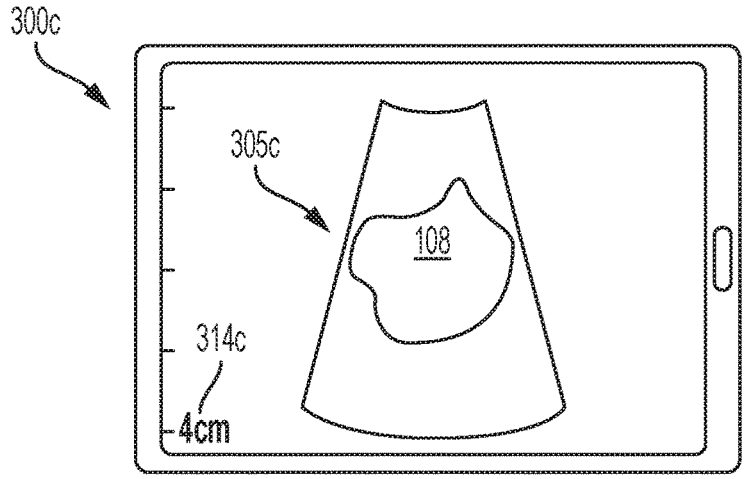

Referring simultaneously to FIG. 3C, shown there generally as 300c is an example view of the ultrasound image feed that has been updated to reflect the imaging depth selected upon release of the continuous contact with the touchscreen. FIG. 3C illustrates the appearance of an example user interface interaction at a point in time after contact with the touchscreen has terminated at the location on the screen last touched in FIG. 3B. In some embodiments, the selection of the imaging parameter may result in transmittal of the selected setting to an ultrasound acquisition unit to cause the ultrasound acquisition unit to modify the live ultrasound image feed, so that the live ultrasound image feed has adjusted imaging parameters that reflect the selected setting. For example, as illustrated in FIG. 3C, the updated ultrasound image feed 305c has an imaging depth of '4 cm' shown by the updated imaging depth indicator 314c. As a result of the imaging depth being altered, the ultrasound image feed 305c of FIG. 3C can allow the entirety of the structure 108 to be viewed (which was only partially viewable in the ultrasound image feed 305a shown in FIGS. 3A and 3B).

As noted, in some embodiments, the ultrasound acquisition unit is configured to transmit and receive ultrasound signals according to an ultrasound sequence. In such embodiments, the selected setting may be used to alter the ultrasound sequence when modifying the imaging parameter. For example, in the example illustrated in FIG. 3C, when modifying the imaging depth, the '4 cm' imaging depth selected upon the release of the drag gesture in FIG. 3B may be transmitted to the ultrasound acquisition unit and the ultrasound acquisition unit may update its ultrasound sequence to modify its frequency and/or focus of the ultrasound energy being transmitted at the '4 cm' imaging depth. By waiting for the release of the drag gesture to reload the ultrasound sequence (e.g., instead of repeatedly updating the ultrasound sequence during generation of the previews in the transitional view), the transitional view may provide a smooth image preview process that avoids the image feed appearing to be jerky.

Figure 4A:
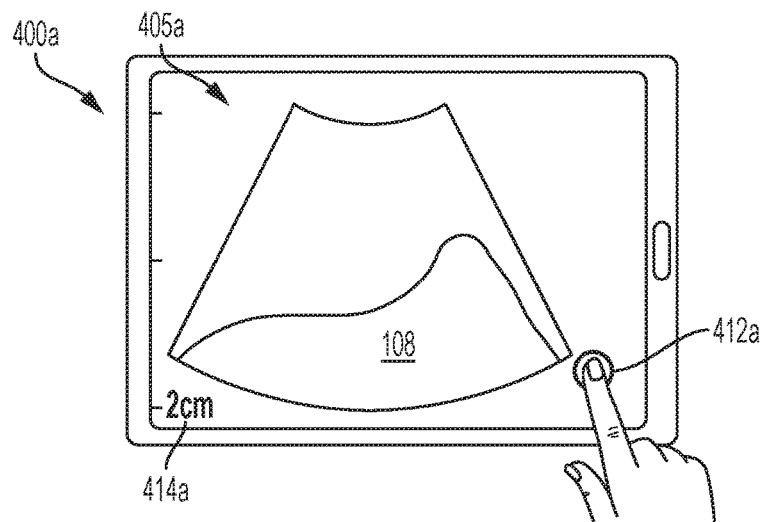
FIGS. 4A-4C are a sequence of user interface interactions for receiving input to decrease the depth imaging parameter during ultrasound imaging, in accordance with at least one embodiment of the present invention.
Figure 4B:
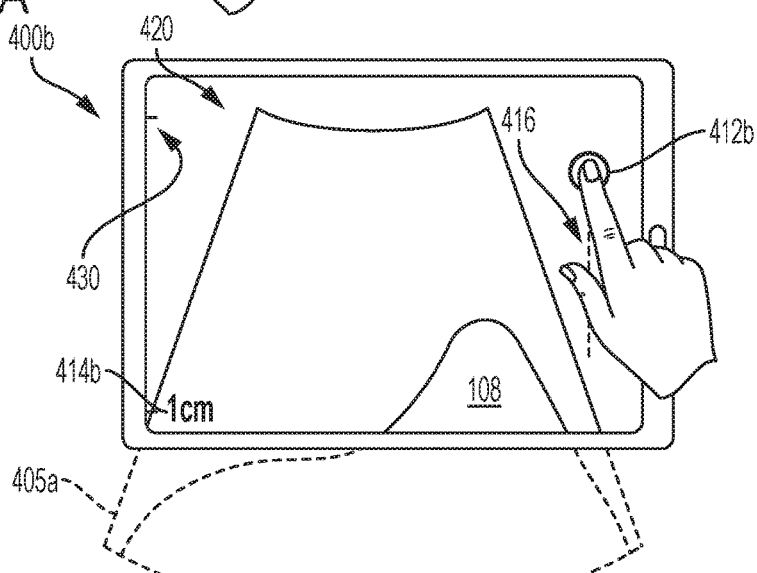
Figure 4C:
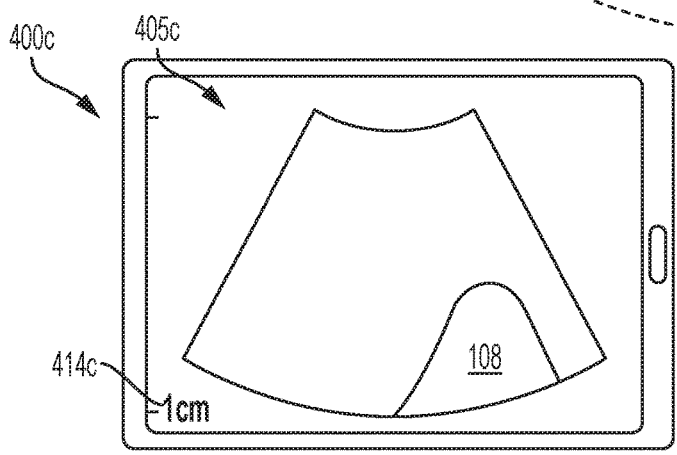

Referring to FIGS. 4A-4C, shown there generally as 400a-400c are a sequence of user interface interactions for receiving input to decrease the depth imaging parameter during ultrasound imaging, in accordance with at least one embodiment of the present invention. Similar to FIGS. 3A-3C, the sequence of user interface interactions shown in FIGS. 4A-4C can be provided in the context of the method of FIG. 2 being performed. In the discussion of FIGS. 4A-4C below, simultaneous reference will also be made to the corresponding acts of FIG. 2.

Referring to FIG. 4A, shown there generally as 400a is the display of an ultrasound image feed 405a showing structure 108 (act 205 in FIG. 2). Similar to FIG. 3A, FIG. 4A provides an imaging depth indicator 414a showing that the imaging depth of the ultrasound image feed 405a is '2 cm'. The imaging depth may be adjusted by touchscreen input that requires continuous contact with the touchscreen. For example, as illustrated in FIG. 4A, such input may be initiated when a touch is received at 412a (act 210 in FIG. 2).

Referring to FIG. 4B, show there generally as 400b is an example transitional view of the ultrasound image feed 405a when adjusting imaging depth of an ultrasound image feed 405a, in accordance with an embodiment of the present invention. FIG. 4B illustrates an example user interface interaction at a point in time after contact with the touchscreen is initiated in FIG. 4A. As illustrated, a drag gesture is initiated in FIG. 4A, and continuous contact with the touchscreen is maintained through the touch path 416 (shown in dotted outline) to touch point 412b. In response, the touchscreen displays a transitional view during the continuous contact that provides previews of the image depth being adjusted (act 215 in FIG. 2).

Referring still to FIG. 4B, the illustrated embodiment may update the appearance of the ultrasound image feed to show a preview 420 of the image depth that corresponds to characteristics of the touch on the touchscreen (act 220 in FIG. 2). For example, the previews 420 of the live ultrasound image feed 405a may include an adjustable scale 430 showing selectable imaging depths which, similar to FIG. 3B, continuously updates in correspondence with a length of the drag gesture. However, since the imaging depth is being decreased in FIG. 4B, the image depth indicator 414b and corresponding preview of the image depth of the live ultrasound image feed may correspondingly decrease (e.g., to show '1 cm') and show the portion of structure 108 that remains viewable.

As with FIG. 3B, in some embodiments, the live ultrasound image feed originally appearing prior to the beginning of the contact with the touchscreen (e.g., image feed 405a from FIG. 4A in the illustrated examples) may continue to be displayed. For example, as the previews 420 show what the projected image depth is expected to be based on the characteristics of the touch, the display of the ultrasound image feed 405a originally viewable in FIG. 4A can be adjusted so that only the portion of that ultrasound image feed 405a matching the depth shown in the imaging depth indicator 414b is shown on the display. As shown in FIG. 4B, the portion of the original ultrasound image feed 405a that no longer is viewable given the preview of the imaging depth (e.g., '1 cm') is shown in dotted outline.

As noted above, when generating the transitional view encompassing the previews 420 and the modified view of the original ultrasound image feed 405a, scan conversion may be repeatedly performed on the image data corresponding to the ultrasound signals, to configure the image data for displaying the previews 420. For example, in the example embodiments illustrated in FIGS. 4A-4B, scan conversion may be repeatedly performed to adapt the image data being acquired: from being displayed on the entirety of the touchscreen in FIG. 4A to only displaying the portion of the ultrasound image feed 405a that aligns with the shallower imaging depth of the preview 420. In some embodiments, such scan conversion may be repeatedly performed without altering the ultrasound sequence of the ultrasound acquisition unit.

The previews 420 of the ultrasound image feed 405a may continue to be updated while there is continuous contact with the touchscreen (the 'NO' branch at act 225 in FIG. 2). However, upon termination of the continuous contact with the touchscreen (the 'YES' branch at act 225 in FIG. 2), a setting for the imaging depth may be selected based on the preview being displayed (act 230 in FIG. 2). In the context of the example scenario discussed with reference to FIG. 4B, upon termination of the drag gesture shown in FIG. 4B, the imaging depth being shown in the adjustable scale 430 and/or the preview 420 (e.g., '1 cm') may be identified as the selected setting for the imaging depth.

Referring simultaneously to FIG. 4C, shown there generally as 400c is an example view of the ultrasound image feed that has been updated to reflect the imaging depth selected upon release of the continuous contact with the touchscreen. FIG. 4C illustrates the appearance of an example user interface interaction at a point in time after contact with the touchscreen has terminated at the location on the screen last touched in FIG. 4B. In some embodiments, the selection of the imaging parameter may result in transmittal of the selected setting to an ultrasound acquisition unit to cause the ultrasound acquisition unit to modify the live ultrasound image feed, so that the live ultrasound image feed has adjusted imaging parameters that reflect the selected setting. For example, as illustrated in FIG. 4C, the updated ultrasound image feed 405c has an imaging depth of '1 cm' shown by the updated imaging depth indicator 414c. As a result of the imaging depth being updated, the ultrasound image feed 405c of FIG. 4C only shows the portion of the structure 108 that remains viewable at the shallower imaging depth. As with the embodiments of FIGS. 3A-3C discussed above, in some embodiments, the selected setting may be used to alter the ultrasound sequence when modifying the live ultrasound image feed.

Referring to FIGS. 3A-3C and 4A-4C, the imaging depth increases or decreases as the user moves from the initial touch point shown in FIG. 3A, 4A to the final release point shown in FIG. 3B, 4B respectively (via the touch paths 316, 416 respectively). To change the depth of the scan and thereby change the ultrasound image feed 305a, 405a from one imaging depth to another, the user places his or her finger(s) on the display and performs a touch gesture to indicate a change in depth via the touchscreen interface. During the touch gesture, previews 320, 420 of the desired imaging depth are shown on the display.

As illustrated in FIGS. 3A-3C and 4A-4C, the gesture involves the user dragging his or her finger(s) in a particular direction to change the depth of the scan. The direction of the drag may be interpreted to determine the direction of the depth change. For example, the touchscreen interface may be configured to interpret a drag gesture having a downward vertical component (e.g., away from the skin line) as signifying an increase in the depth (FIGS. 3A-3C), and a drag gesture having an upward vertical component (e.g., toward the skin line) as signifying a decrease in the depth (FIGS. 4A-4C). Thus, to move from initial imaging depth shown in FIG. 3A, 4A to the transitional views shown in FIGS. 3B, 4B respectively, the user may drag his or her finger(s) downward or upward (as the case may be) on the screen a certain distance.

In some embodiments, the characteristics of the touch gesture may be measured in the display space. For example, the length of the touch paths 316, 416 may be defined as the distance between the point at which the finger(s) makes contact with the screen at 312*a*, 412*a* respectively and the point on the screen at which the drag is released 312*b*, 412*b* respectively. A longer drag may be interpreted to cause a relatively larger change in depth than for a shorter drag. The user may maintain tactile contact of his/her fingers with the display screen while moving through one or more transitional views 320, 420 on the display (by adjusting the depth upward and/or downward by way of using touch gestures) before lifting his or her finger(s) to view the desired target anatomy in the final view shown in FIGS. 3C, 4C respectively.

As discussed in greater detail below with respect to FIG. 10, in some embodiments, instead of or in addition to identifying a selected setting upon release of a touch gesture (e.g., at 312*b*, 412*b* of FIGS. 3B, 4B respectively), a selected setting for the imaging parameter can be identified when the finger pauses or stops moving for a predetermined period of time (even if contact with the touchscreen remains). For example, in such embodiments, act 225 of FIG. 2 may be configured to determine a length of pause and continue to act 230 if the pause exceeds the predetermined amount of time.

As noted, the transitional views may also be configured to display (at the same time) the original ultrasound image feeds 305*a*, 405*a* of FIGS. 3A and 4A respectively. For example, this may allow the user to visually compare the original ultrasound image feed 305*a*, 405*a* and their respective previews 320, 420 to determine if the adjustment in imaging depth results in a higher quality image or is closer to displaying the target anatomy. Different ways of delineating the original ultrasound image feed 305*a*, 405*a* from the projections offered by the previews 320, 420 may be possible. For example, the display may be configured to display a line signifying the boundary/depth of the original ultrasound image feeds 305*a*, 405*a*, and/or display the previews 320, 420 in a different color. Additionally or alternatively, highlighting, shading or manners of visual distinction from the original ultrasound image feed 305*a*, 405*a* may be possible.

As discussed above, an updated penetration depth and/or an updated focal depth may be determined in accordance with the touch input. As will be understood by persons skilled in the art, the penetration depth may be based in part on the tissue type, and the focal depth may be based on the transmit beamforming. The image quality and resolution is generally best at the focal depth, which is the distance between the transducer and the focal zone. After the setting for the imaging depth image parameter has been selected, the focal depth of the ultrasound image feed may thus be updated.

While the example embodiments discussed above have been with respect to the use of a drag gesture to modify image depth, other interpretations or configurations are possible in other embodiments. For example, the extent of the change of depth may be based on other characteristics of other touch gestures, such as the pressure of the touch in pressure-sensitive touchscreen interfaces, the timing or speed of the touch, the location/position of the finger(s) on the display screen, and/or the like.

Referring to FIGS. 5A-5D, shown there generally as 500*a*-500*d* are a sequence of user interface interactions for receiving input to flip an ultrasound image along a vertical axis during ultrasound imaging, in accordance with at least one embodiment of the present invention. FIGS. 5A-5D illustrates another way the method of FIG. 2 may be performed. As a result, the discussion below will again be made with simultaneous reference to the acts of FIG. 2.

When scanning using an ultrasound probe or scanner, one side of the probe or scanner may be provided with a notch, bump or other physical or visual cue that provides an indication of orientation. The displays of ultrasound systems typically provide a corresponding visual indicator (e.g., a colored dot) for this physical cue on the ultrasound probe or scanner. Depending on the medical application, the probe orientation with respect to the patient and/or such on-screen visual indicator may differ.

For example, for general medical examinations, when scans are performed along the longitudinal or coronal plane, it is conventional to orient the physical cue on the probe or scanner towards a patient's head. For scans along the transverse plane, it is conventional in general medical examinations to orient the physical cue towards the right side of the patient. These scans are typically displayed with the visual indicator on the left side of the screen of an ultrasound system. This is because a general medical (e.g., gynecologic) ultrasound examination may be performed by an ultrasound operator approaching the patient from the patient's right side or an inferior position, so that the visual indicator being on the left side of the screen aligns with the ultrasound operator's view of the patient.

However, despite this generic ultrasound convention, the use of ultrasound in certain medical applications (e.g., cardiac) have developed different conventions. For example, since cardiac imaging is typically performed by the ultrasound operator approaching the patient from the patient's left side (due to the position of the heart being on the left half of the patient's body), traditional cardiology orientation typically positions the visual indicator on the right side of the screen so as to align with the ultrasound operator's view of the patient when they approach the patient from the patient's left side.

Traditional ultrasound systems may provide controls that allow the flipping of an ultrasound image along a vertical axis, for example, so as to allow the visual indicator to be positioned on the left or right side of the screen as desired. As noted above with respect to FIGS. 1A and 1C, simple 'left' or 'right' buttons 116, 118 may not clearly indicate what their purpose is (e.g., if the visual indicator is on the left side of the screen, it is unclear whether the pressing of a 'left' button 116 results in rotation of the ultrasound image so that the visual indicator will be on the right side of the screen or whether the pressing of such button will confirm that the visual indicator should be placed on the left side of the screen without further flipping the image).

Figure 5A:
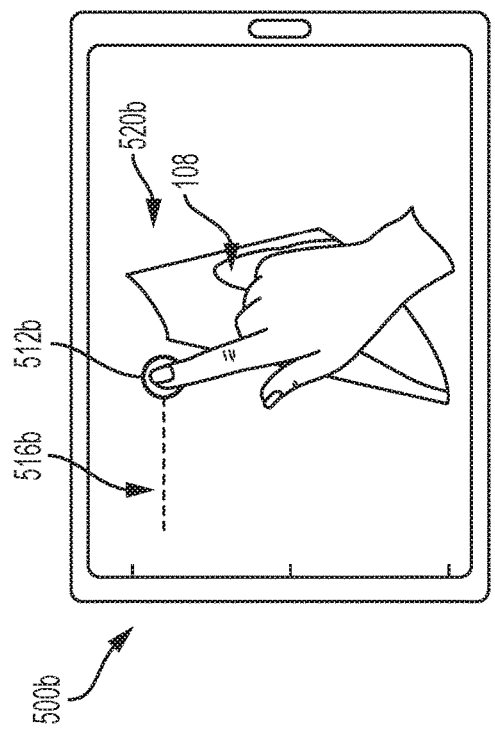
FIGS. 5A-5D are a sequence of user interface interactions for receiving input to rotate an ultrasound image during ultrasound imaging, in accordance with at least one embodiment of the present invention.

Referring to FIG. 5A, shown there generally as 500*a* is the display of a live ultrasound image feed 505*a* showing structure 108 (act 205 in FIG. 2), in accordance with an embodiment of the present invention. The display may provide a visual indicator that corresponds to the position of a physical orientation cue on the ultrasound scanner or probe. In the illustrated embodiments, this visual indicator may be touched and dragged using a drag gesture to modify the orientation of the ultrasound image feed 505*a*. In FIG. 5A, the visual indicator is not viewable as it is under the touch point 512*a*. The beginning of this touch input may constitute act 210 in FIG. 2.

Figure 5B:
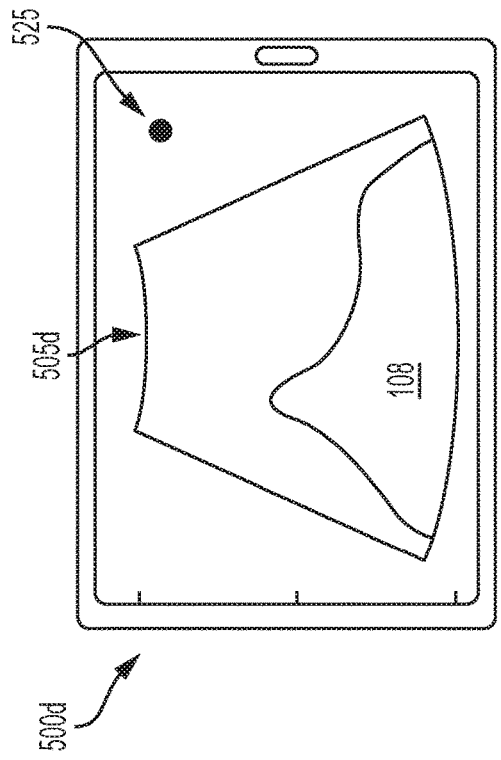

Referring to FIG. 5B, shown there generally as 500*b* is an example transitional view of the ultrasound image feed 505*a* shown in FIG. 5A, in accordance with an embodiment of the present invention. In some embodiments, the continuous contact with the touchscreen corresponds to a drag gesture, and the previews of the live ultrasound image feed may be an animation from a pre-flipped orientation of the live ultrasound image feed to a flipped orientation of the live ultrasound image feed. FIG. 5B illustrates an example user interface interaction at a point in time after contact with the touchscreen is initiated in FIG. 5A. As illustrated, a drag gesture is initiated in FIG. 5A to touch point 512b, and continuous contact with the touchscreen is maintained through the touch path 516b (shown in dotted outline). In response, the touchscreen may display a transitional view 520b during the continuous contact that provides previews of the of the flipping of the ultrasound image along the vertical axis (act 215 in FIG. 2).

In some embodiments, the transitional view may be continuously updated to correspond to characteristics of the contact with the touchscreen. For example, this may include the animation from a pre-flipped orientation to a flipped orientation being continuously updated to correspond with a length of the drag gesture. Referring still to FIG. 5B, the illustrated example embodiment may update the appearance of the preview 520b to rotate in a manner that corresponds to characteristics of the touch on the touchscreen (act 220 in FIG. 2). For example, the degree of rotation may depend on the distance the visual indicator is from the center of the display during the drag gesture. As illustrated, the previews 520b of the live ultrasound image feed 505a may not completely rotate to the orientation where the visual indicator is on the right side of the screen. Rather, the rotation may only proceed partially as the drag gesture is initiated to suggest to the user the type of imaging parameter being adjusted. As shown in FIG. 5B, the structure 108 remains viewable during this transitional view.

In some embodiments, the live ultrasound image feed originally appearing prior to the beginning of the contact with the touchscreen (e.g., image feed 505a from FIG. 5A) may continue to be displayed. For example, as the previews 520b show the partial rotation along the vertical axis corresponding to the extent of the drag gesture, it may continue to show the live image data from the ultrasound image feed 505a.

Figure 5C:
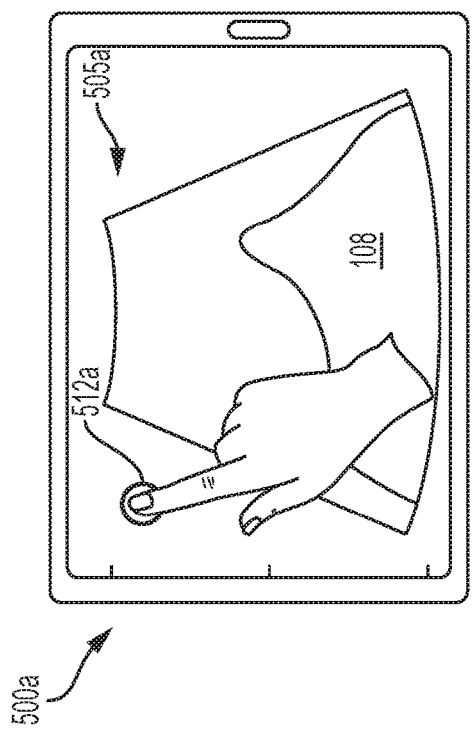

Referring to FIG. 5C, shown there generally as 500c is a further example transitional view of the ultrasound image feed 505a shown in FIG. 5A, in accordance with an embodiment of the present invention. FIG. 5C illustrates an example user interface interaction at a point in time after FIG. 5B. As illustrated, the previews 520c of the ultrasound image feed 505a may continue to be updated while there is continuous contact with the touchscreen (the 'NO' branch at act 225 in FIG. 2). For example, as the drag gesture proceeds from touchpoint 512b shown in FIG. 5B through touch path 516c (as shown in dotted outline) to touch point 512c, it can be seen that the preview 520c shows the ultrasound image feed continuing to rotate past the midpoint of the rotation. Specifically, it can be seen that the protrusion of structure 108 which was on the right side of the ultrasound image in FIGS. 5A and 5B has now been rotated so that it is on the left side of the ultrasound image in FIG. 5C.

As noted above, when generating the transitional view encompassing the previews 520b, 520c and the modified version of the original ultrasound image feed 505a of FIG. 5A, scan conversion may be repeatedly performed on the image data from the ultrasound signals to configure the image data for displaying the previews 520b, 520c of the live ultrasound image feed 505a. For example, in FIGS. 5A-5D, scan conversion may be repeatedly performed to adapt the image data being acquired: from being displayed in a pre-flipped orientation of FIG. 5A to only displaying the image data in a partially-flipped manner shown in FIGS. 5B and 5C. In some embodiments, such scan conversion may be repeatedly performed without altering the ultrasound sequence being used by the ultrasound acquisition unit to acquire image data.

Referring still to FIG. 5C, upon termination of the continuous contact with the touchscreen (the 'YES' branch at act 225 in FIG. 2), a setting for the image orientation may be selected based on the preview being displayed (act 230 in FIG. 2). For example, in the context of the example scenario discussed with reference to FIG. 5C, the orientation of the ultrasound image feed displayed upon the release of the touch may depend on the extent to which the ultrasound image feed 505a of FIG. 5A is rotated in the preview 520c. For example, if the drag gesture terminates at touch point 512c, the display of the ultrasound image feed may "snap" to the orientation where the visual indicator for the physical cue on the ultrasound probe is positioned on the right of the screen.

Figure 5D:
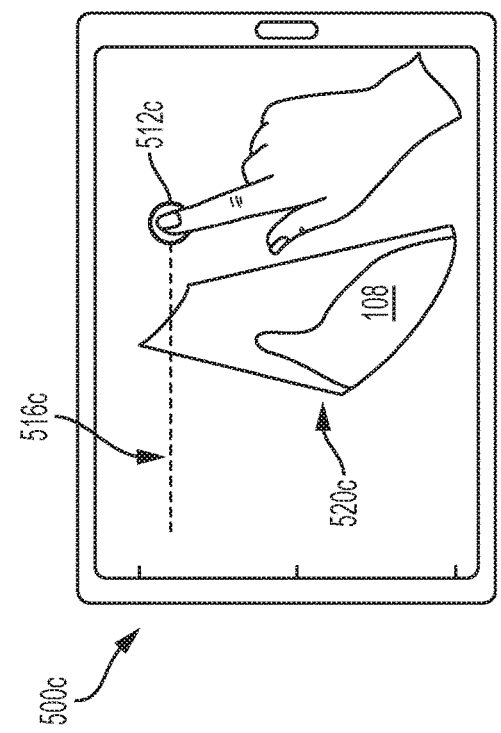

Referring to FIG. 5D, shown there generally as 500d is an example view of the ultrasound image feed that has been updated to reflect the change in orientation upon release of the continuous contact with the touchscreen, in accordance with an embodiment of the present invention. As can be seen, the visual indicator 525 (previously covered by a finger in FIGS. 5A-5C) is now positioned on the right side of the screen and the protrusion in the structure 108 formerly on the right side of the ultrasound image feed 505a shown in FIG. 5A is now shown on the left side of the ultrasound image feed 505d of FIG. 5D.

Figure 6:
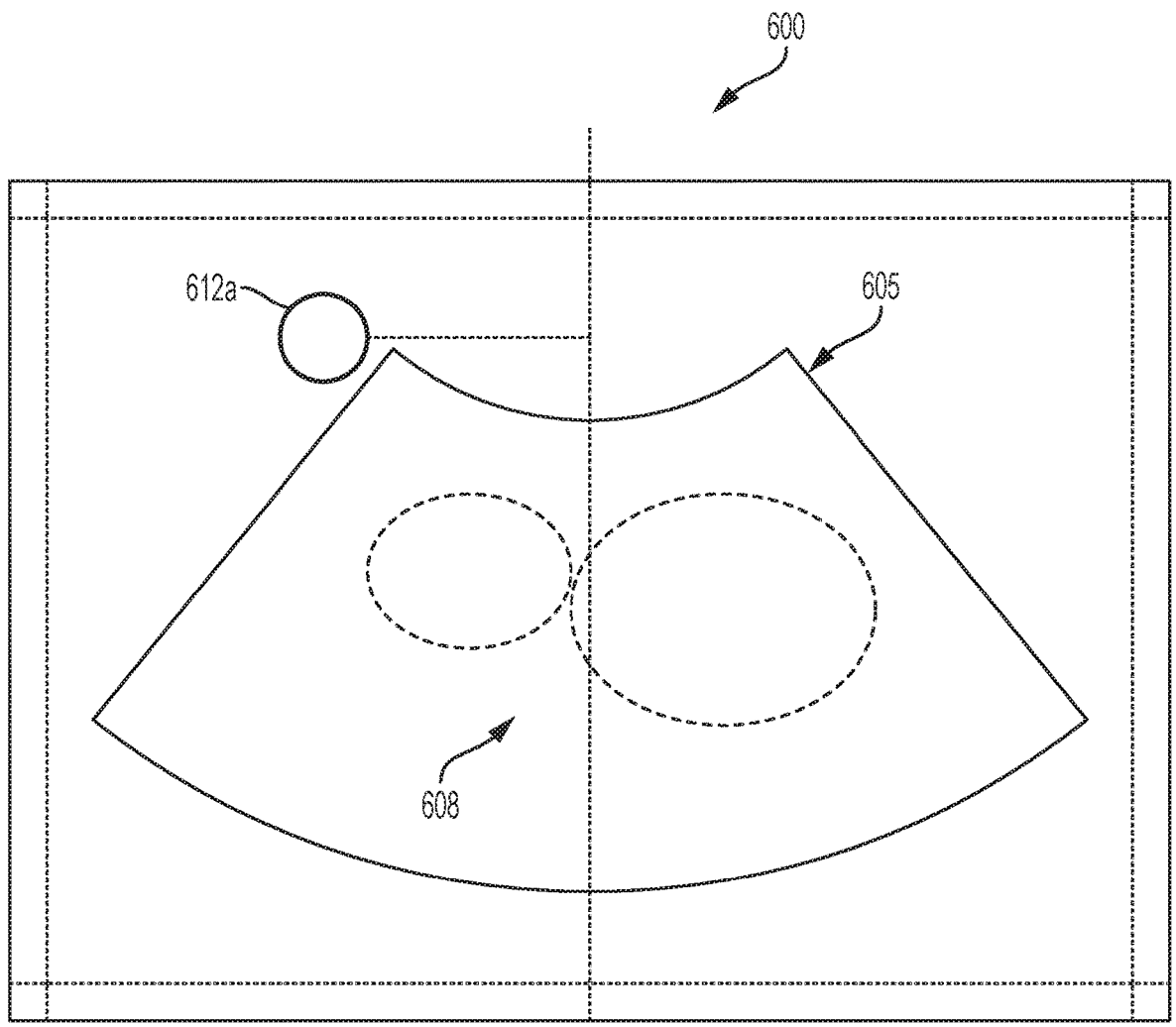
FIG. 6 is a diagram illustrating operation of the input to rotate an ultrasound image, in accordance with at least one embodiment of the present invention.

Referring to FIG. 6, shown there generally as 600 is a diagram illustrating operation of the input to rotate an ultrasound image, in accordance with at least one embodiment of the present invention. As illustrated, another example display of an ultrasound image 605 is shown with structures 608. As noted with reference to FIG. 5A above, a horizontal drag gesture may be initiated at touch point 612a (e.g., touching and dragging a visual indicator that corresponds to the physical orientation cue on the ultrasound probe). If the drag gesture is released before the drag gesture is made past the vertical dotted line bisecting the ultrasound image 605, the animation may "snap" back to the original orientation that was being viewed prior to the initiation of the drag gesture. For example, in the example embodiment illustrated in FIGS. 5A-5D, this may happen if the drag gesture is released at the point shown in FIG. 5B. However, as noted, if the drag gesture is made past the center vertical line bisecting the ultrasound image feed 605 and released thereafter, the orientation of the image may "snap" to the orientation where the visual indicator is on the right side of the screen. As noted above, in some embodiments, the degree of rotation may depend on the distance of the indicator from the center of the display during the drag gesture.

The embodiments discussed in FIGS. 5A-5D and 6 have been discussed with respect to the flipping of an ultrasound image feed 605 from an orientation where the visual indicator is on the left side of the screen to where the visual indicator is on the right side of the screen. However, embodiments where the orientation is changed from the visual indicator being on the right side of the screen to the left side of the screen may be performed in a similar manner.

The embodiments for flipping of an image along a vertical axis may be employed with any ultrasound system with a touchscreen display. However, such embodiments may be particularly desirable in portable ultrasound systems that use the same probe for multiple types of medical examinations (e.g., general, abdomen, and cardiac). As noted, general ultrasound scanning convention positions the on-screen visual orientation indicator on the left side of the screen; however, the convention for cardiac applications position the visual orientation indicator on the right side of the screen. In traditional ultrasound systems with multiple probes, the display of the ultrasound system may be automatically configured to display the orientation of the visual indicator based the probe type attached. For example, when a cardiac probe is attached to a traditional system, the system may automatically orient the image so that the visual indicator is on the right side of the screen. In contrast, if other non-cardiac types of probes are attached, then the ultrasound system may automatically orient the image so that the visual indicator is on the left side of the screen. Due to this automatic configuration of visual indicator orientation, the button-based controls for flipping an orientation along a vertical axis may not be used as frequently as some other controls. As a result, the shortcomings associated therewith may not be as readily apparent.

However, in a portable ultrasound system that configures the same transducer to operate in multiple modes (e.g., as may be enabled by embodiments described in U.S. patent application Ser. No. 15/207,203, which is incorporated herein by reference), the same ultrasound transducer may potentially be used to perform both abdominal and cardiac imaging within the same examination. As a result, the orientation modification controls may need to be used more frequently in such portable ultrasound systems, and the benefits of the embodiments described herein for modifying orientation may be more significant.

The example embodiments discussed in the context of FIGS. 5A-5D and 6 are for flipping the live ultrasound image feed along a vertical axis. However, in additional or alternative embodiments, the live ultrasound image feed may also be similarly flipped along a horizontal axis so that the ultrasound image feed appears "upside-down" (e.g., with the image depth increasing from the bottom of the image towards the top instead of increasing from the top of the image towards the bottom). Such image orientation may be used in certain medical applications (e.g., urology).

In some embodiments, the flipping of the ultrasound image along a horizontal axis may be performed in a manner similar to the flipping along the vertical axis. For example, the visual indicator may be touched and dragged in a vertical direction to flip the ultrasound image along the horizontal axis. The image may similarly be updated to provide a transitional view with previews that updates in accordance with characteristics of the touchscreen contact. For example, if the drag is in a vertical direction, the image may begin to rotate along the horizontal axis partially as the drag gesture is initiated to suggest to the user the type of imaging parameter being adjusted. Also, similar to the flipping along the vertical axis, the flipping of the ultrasound image feed along a horizontal axis may also "snap" back to the original orientation or the upside-down orientation, depending on whether the drag has caused the preview to be rotated to, respectively, before the midpoint of the rotation or past the midpoint of the rotation.

Figure 7A:
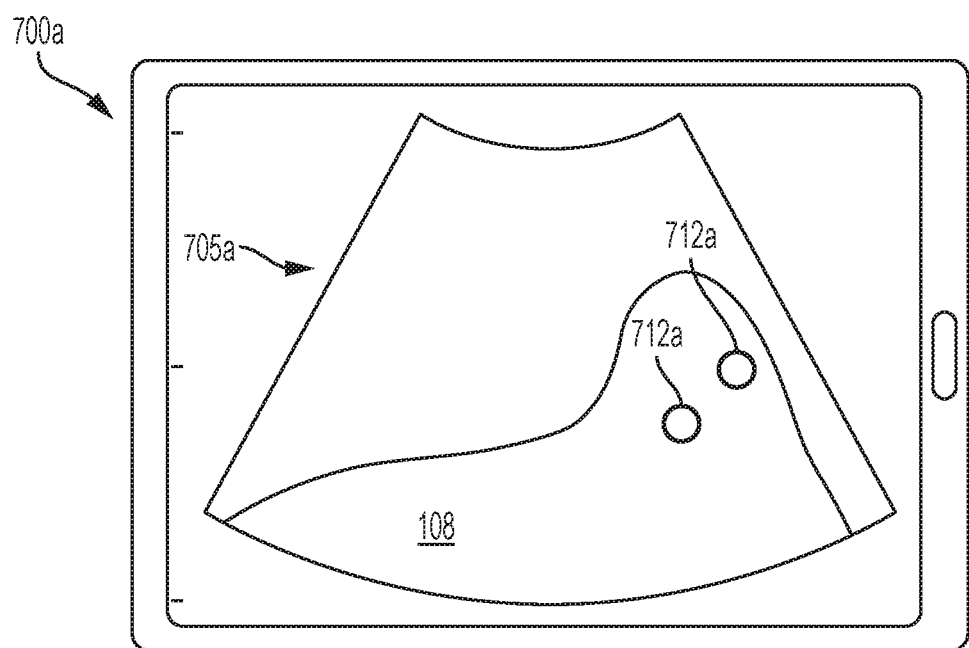
FIGS. 7A-7C are a sequence of user interface interactions for receiving input to perform a high-definition (HD) zoom during ultrasound imaging, in accordance with at least one embodiment of the present invention.
Figure 7B:
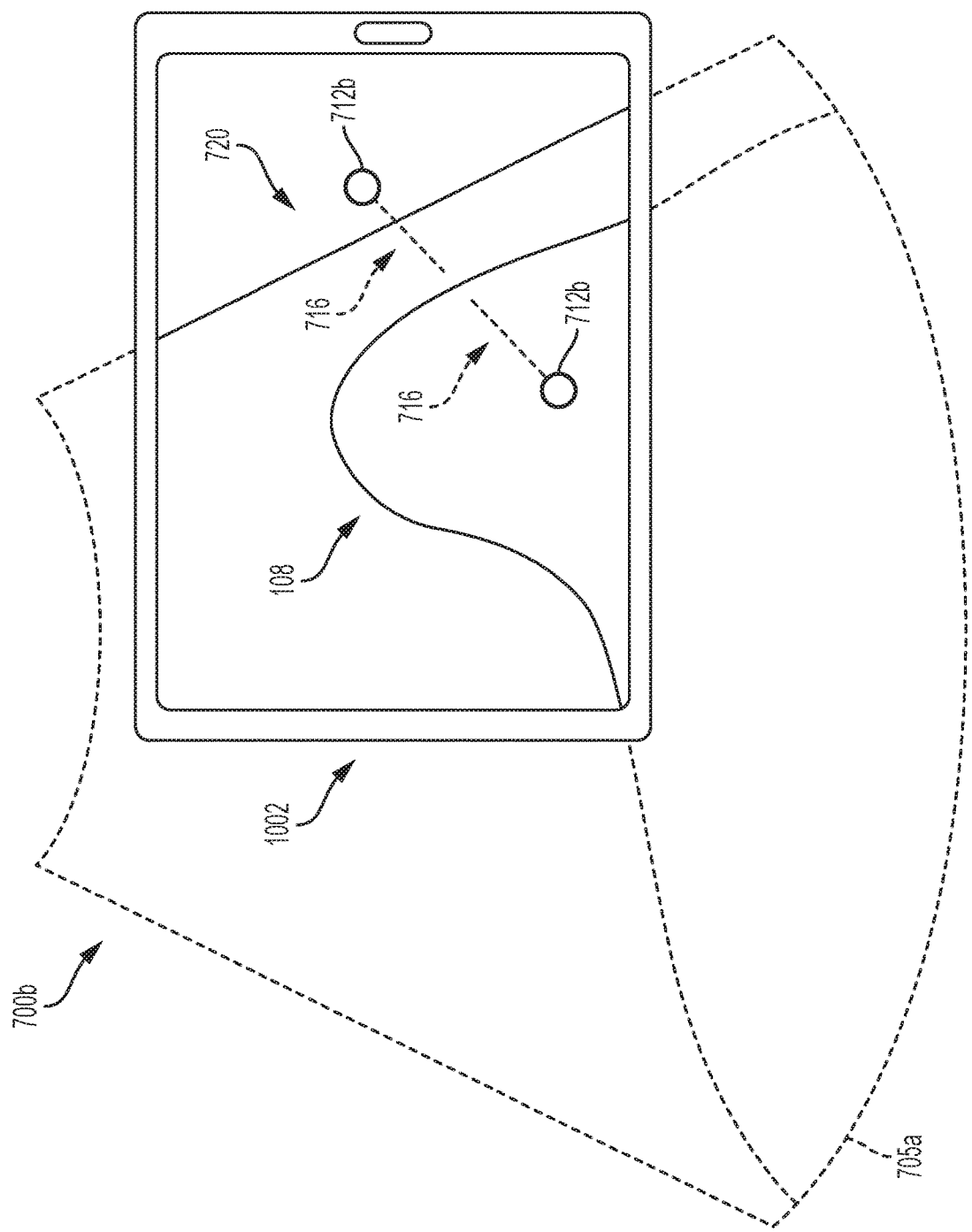
Figure 7C:
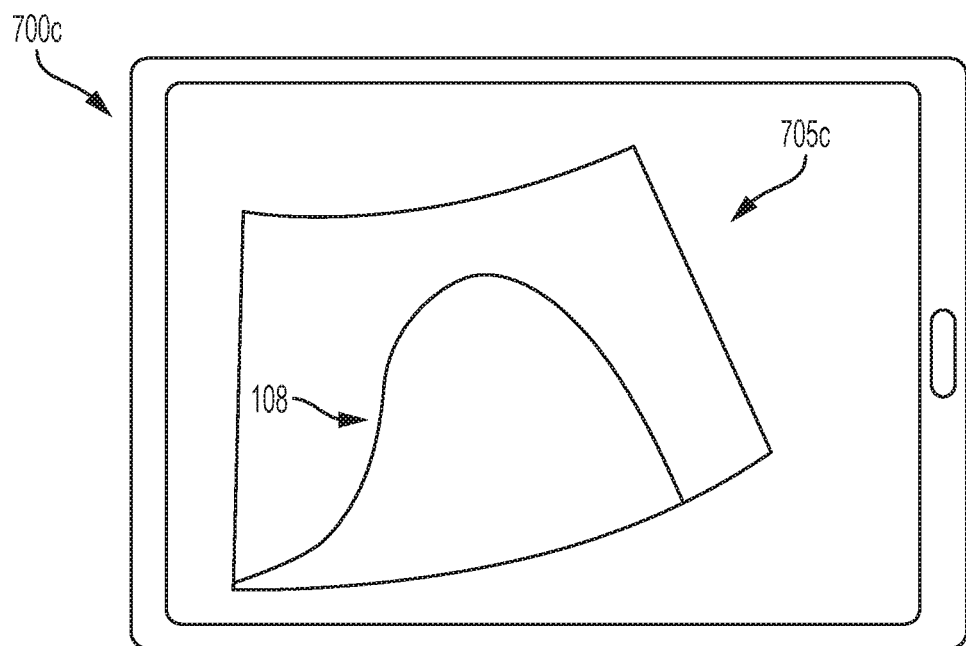

Referring to FIGS. 7A-7C, shown there generally as 700a-700c are a sequence of user interface interactions for receiving input to perform a high-definition (HD) zoom during ultrasound imaging, in accordance with at least one embodiment of the present invention. FIGS. 7A-7C illustrate another embodiment of the performance of the method of FIG. 2; and the discussion below will also be made with reference to the acts of FIG. 2.

As noted above with reference to FIG. 1D, ultrasound imaging systems may generally provide a read zoom operation (which allows magnification of a part of the image using existing image data) and a write zoom operation (which provides higher resolution zoom by updating the ultrasound sequence to focus scanning to an identified ROI). When positioning the ROI box for the write zoom operation, traditional ultrasound systems may provide a user interface that receives input using a trackball or directional buttons to position a ROI box. In examples where touchscreen buttons are used, positioning the ROI box may require repeated pressing of directional buttons that each cause an updating of the ultrasound sequence. This may cause the screen to jump and flicker as the image data is reloaded with each successive button press.

Referring to FIG. 7A, shown there generally as 700a is the display of a live ultrasound image feed 705a showing structure 108 (act 205 in FIG. 2), in accordance with an embodiment of the present invention. As illustrated, there may be a protrusion in the structure 108 that is viewable in the ultrasound image feed 705a. An ultrasound operator may wish to perform a write zoom operation to obtain a higher resolution view of such protrusion. In the present embodiments, to initiate a write zoom operation, the touchscreen may be configured to receive input for creating a ROI box for use in a write zoom operation on the live ultrasound image feed 705a. In the illustrated embodiment, this input may be a pinch gesture that is initiated with multiple touches at touchpoints 712a. The beginning of this touch input may constitute act 210 in FIG. 2. The circles for touch points shown in FIGS. 7A, 7B, 8A, 8B, 9A, and 9B are provided to show the locations of touch points, and may not actually be shown on the display.

Referring to FIG. 7B, shown there generally as 700b is an example transitional view of the ultrasound image feed 705a shown in FIG. 7A, in accordance with an embodiment of the present invention. FIG. 7B illustrates an example user interface interaction at a point in time after contact with the touchscreen is initiated in FIG. 7A. As illustrated, the continuous contact with the touchscreen corresponds to a pinch gesture. For example, a pinch-out gesture is initiated from touchpoints 712a in FIG. 7A and extended to touchpoints 712b in FIG. 7B; and the continuous contact with the touchscreen may be maintained through the touch paths 716. In response, the touchscreen may display a transitional view 720 during the continuous contact that provides previews of the desired ROI box for the write zoom operation (act 215 in FIG. 2).

Referring still to FIG. 7B, the illustrated example embodiment may update the appearance of the previews 720 in a manner that corresponds to characteristics of the touch on the touchscreen (act 220 in FIG. 2). For example, this may include the previews 720 of the live ultrasound image feed 705a being continuously updated to provide a zoomed-in view, with the level of zoom increasing with the length of the pinch-out gesture. As noted above, when generating the transitional view encompassing the previews 720, scan conversion may be repeatedly performed on the image data from the ultrasound signals to configure the image data for displaying the previews 720 of the live ultrasound image feed. In some embodiments, such scan conversion may include repeatedly performing read zoom operations on the image data of the live ultrasound image feed 705a, so as to read existing image data without updating or reloading the ultrasound sequence and only show the zoomed-in portion of the ultrasound image feed 705a that can be viewed on the display unit 1002. For example, as illustrated in FIG. 7B, the preview 720 is a zoomed-in view of the ultrasound image feed 705a which is shown in FIG. 7A, with the remaining portion of the original ultrasound image feed 705a that extends beyond the edges of the viewable area of the screen being shown in dotted outline. For example, in FIG. 7B, an ultrasound operator may be using the pinch-out gesture to create a ROI box to focus on the protrusion in the structure 108 viewable in the original ultrasound image feed 705a.

In some embodiments, the live ultrasound image feed originally appearing prior to the beginning of the contact with the touchscreen (e.g., image feed 705a from FIG. 7A in the illustrated examples) may continue to be displayed. For example, as the previews 720 showing the ROI box for the write zoom operation are being displayed, data from the live ultrasound image feed 705a may continue to be displayed. For example, if there is motion in the protrusion of the structure 108, the previews 720 viewable during the continuous contact with the touchscreen may continue to show this motion as the previews 720 are being generated and displayed in FIG. 7B.

Referring still to FIG. 7B, the previews 720 of the ultrasound image feed 705a may continue to be updated while there is continuous contact with the touchscreen (the 'NO' branch at act 225 in FIG. 2). However, upon termination of the continuous contact with the touchscreen (the 'YES' branch at act 225 in FIG. 2), a setting for the write zoom operation may be selected based on the preview being displayed (act 230 in FIG. 2). For example, in the context of the example scenario discussed with reference to FIG. 7B, the zoomed-in image viewable upon the release of the touch may constitute the ROI box on which the write zoom operation is to be performed.

Referring to FIG. 7C, shown there generally as 700c is an example view of the ultrasound image feed that has been updated after the write zoom operation based on the ROI box preview shown in FIG. 7B, in accordance with an embodiment of the present invention. As can be seen, the ultrasound image feed 705c of FIG. 7C shows a zoomed-in view of the ultrasound image feed 705a in FIG. 7A, highlighting the protrusion of structure 108. To complete the write zoom operation, the selected parameters of the ROI Box shown in the preview 720 of FIG. 7B may be used to alter the ultrasound sequence of the transducer array of the ultrasound acquisition unit, so as to focus additional ultrasound signal lines in the direction and at the depth indicated by the ROI box.

The embodiments described in FIGS. 7A-7C provide a mechanism to allow selection of an ROI box for a write zoom operation without the delays and/or inefficiencies associated with rotating a track ball or the pressing of directional buttons repeatedly. It may also avoid the jumps and screen flickering caused by directional buttons that cause the ultrasound sequence to reload after every press. For example, by first performing a read zoom operation using existing image data acquired using an existing ultrasound sequence, the read zoom operation can provide a smooth transition to preview the ROI box.

While the embodiments of FIGS. 7A-7C have been discussed with respect to a pinch-out gesture performing a zoom-in operation to identify an ROI box for a HD zoom operation, it will be understood that the described embodiments may also be used to identify an ROI box for other ultrasound modes such as Doppler. In further embodiments, a pinch gesture may also be used to help identify zoomed-in area on which to select the M line in M-mode operation.

In various embodiments, a pinch-in gesture may be used in an analogous manner to modify the size of the ROI box. For example, once the image is in a zoomed-in state, a pinch-in gesture may be used to expand the size of the ROI box. Once the pinch-in gesture is released, the ultrasound sequence may be updated to reflect the ROI box, and the HD zoom may be performed again.

Figure 8A:
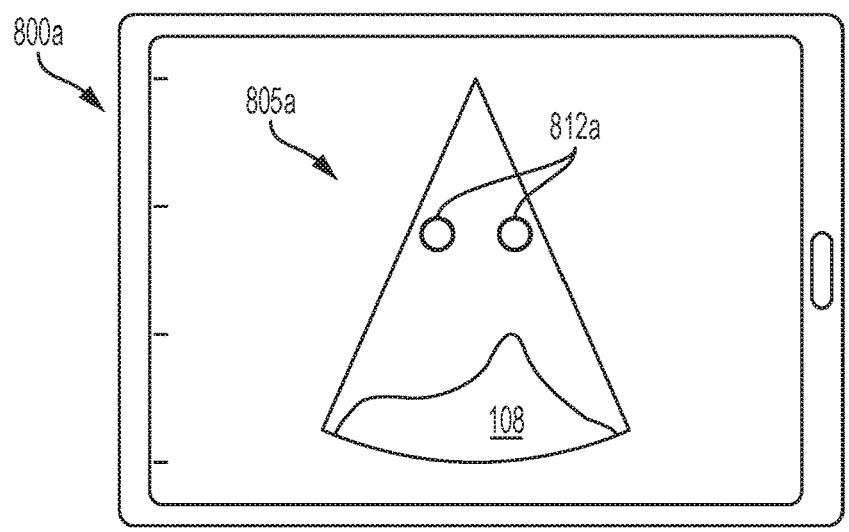
FIGS. 8A-8C are a sequence of user interface interactions for receiving input to increase the sector angle of a sector image during ultrasound imaging, in accordance with at least one embodiment of the present invention.
Figure 8B:
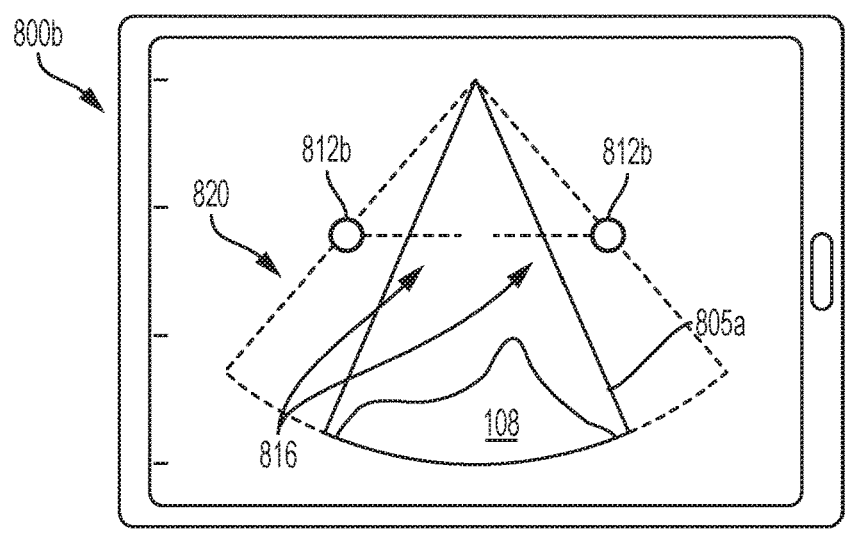
Figure 8C:
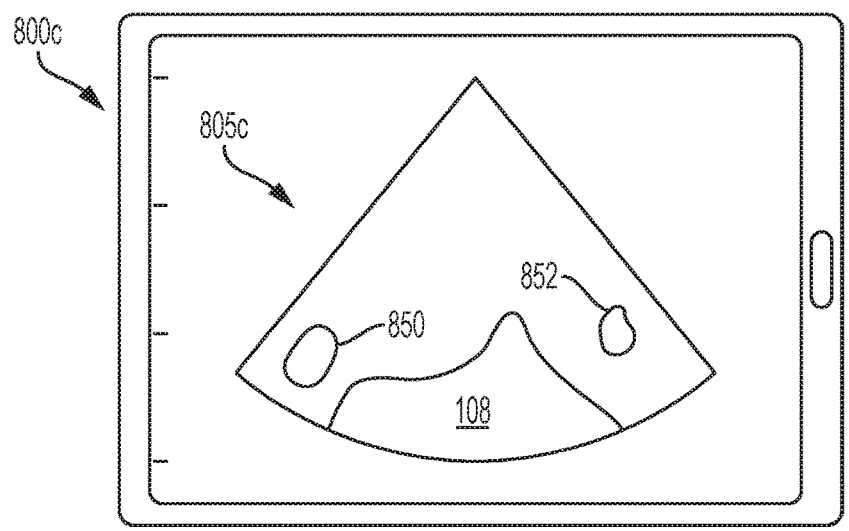

Referring to FIGS. 8A-8C, shown there generally as 800a-800c are a sequence of user interface interactions for receiving input to increase the sector angle of a sector image during ultrasound imaging, in accordance with at least one embodiment of the present invention. FIGS. 8A-8C illustrate an embodiment of the performance of the method of FIG. 2; and the discussion below will again be made with reference to the acts of FIG. 2.

As noted above with reference to FIG. 1D, ultrasound systems may allow imaging with transducers that emit and receive ultrasound signals in a phased (e.g., sweeping) manner across a range of directions. This creates an ultrasound image feed having a sector image shape. The sector angle parameter may control the range of directions and thus the sector angle of the sector image. When altering the sector angle of a sector image, traditional ultrasound operations may provide buttons (e.g., the '+' and '−' buttons 120, 122 shown in FIG. 1D) that require repeated pressing that, with each press, cause an updating of the ultrasound sequence. Similar to the other imaging parameters discussed herein, this may cause the screen to jump and flicker with each successive ultrasound sequence update.

Referring to FIG. 8A, shown there generally as 800a is the display of a live ultrasound image feed 805a showing structure 108 (act 205 in FIG. 2), in accordance with an embodiment of the present invention. An ultrasound operator may wish to increase the sector angle of the sector image being displayed. In the present embodiments, the touchscreen may be configured to receive a pinch gesture input for increasing the sector angle. As illustrated, the two touch points for the pinch gesture may be initiated at touchpoints 812a. The beginning of this touch input may constitute act 210 in FIG. 2.

Referring to FIG. 8B, shown there generally as 800b is an example transitional view of the ultrasound image feed 805a shown in FIG. 8A, in accordance with an embodiment of the present invention. For example, FIG. 8B illustrates an example user interface interaction at a point in time after contact with the touchscreen is initiated in FIG. 8A. In some embodiments, the continuous contact with the touchscreen corresponds to a pinch gesture. As illustrated, a pinch-out gesture is initiated from touchpoints 812a in FIG. 8A and extended to touchpoints 812b in FIG. 8B; and continuous contact with the touchscreen may be maintained through the touch paths 816 (shown in dotted outline in FIG. 8B). In response, the touchscreen may display a transitional view during the continuous contact that provides previews 820 of the desired sector angle for the sector image (act 215 in FIG. 2).

Referring still to FIG. 8B, the illustrated example embodiment may update the appearance of the ultrasound image feed to show previews 820 of the sector angle that correspond to characteristics of the touch on the touchscreen (act 220 in FIG. 2). As illustrated, this may include the previews 820 of the live ultrasound image feed 805a being continuously updated to provide an outline of the increased sector angle (shown in dotted outline in FIG. 8B), and the outline may increase with the length of the pinch-out gesture.

In some embodiments, the live ultrasound image feed originally appearing prior to the beginning of the contact with the touchscreen (e.g., image feed 805a from FIG. 8A in the illustrated examples) may continue to be displayed. For example, as the previews 820 showing the desired sector angle are being shown, data from the live ultrasound image feed 805a may continue to be displayed. For example, the structure 108 may continue to be viewable and displayed as the previews 820 are being generated and displayed in FIG. 8B.

Referring still to FIG. 8B, the previews 820 of the ultrasound image feed 805a may continue to be updated while there is continuous contact with the touchscreen (the 'NO' branch at act 225 in FIG. 2). However, upon termination of the continuous contact with the touchscreen (the 'YES' branch at act 225 in FIG. 2), a setting for the sector angle imaging parameter may be selected based on the preview being displayed (act 230 in FIG. 2). For example, in the context of the example scenario discussed with reference to FIG. 8B, the sector angle indicated by the preview 820 being displayed may be selected to be the desired sector angle.

Referring to FIG. 8C, shown there generally as 800c is an example view of the ultrasound image feed that has been updated after the sector angle imaging parameter has been modified based on preview shown in FIG. 8B, in accordance with an embodiment of the present invention. To confirm the selection of the sector angle, the selected parameters for the sector angle shown in the preview 820 of FIG. 8B may be used to alter the ultrasound sequence of the transducer array in an ultrasound acquisition unit, so as to expand the range of angles for the ultrasound signals being emitted and received by the ultrasound transducer. As can be seen, the ultrasound image feed 805c of FIG. 8C shows an updated ultrasound image feed that has a wider sector angle. In this wider-angle sector image, not only can the structure 108 be seen, but additional structures 850, 852 previously not viewable in the narrower sector angle of FIG. 8A or 8B become viewable.

Figure 9A:
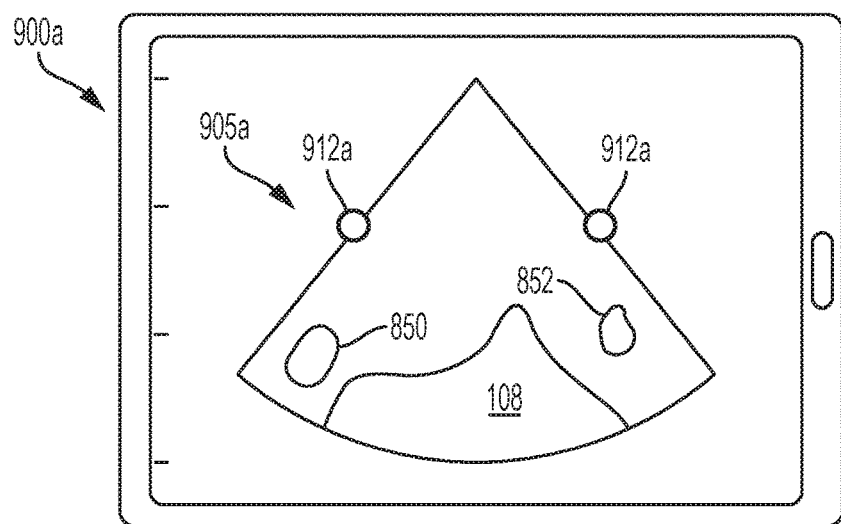
FIGS. 9A-9C are a sequence of user interface interactions for receiving input to decrease the sector angle of a sector image during ultrasound imaging, in accordance with at least one embodiment of the present invention.
Figure 9B:
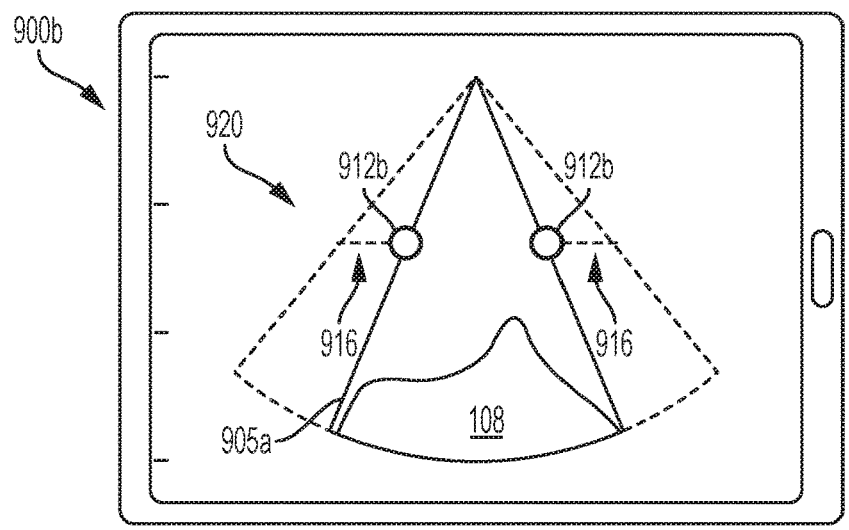
Figure 9C:
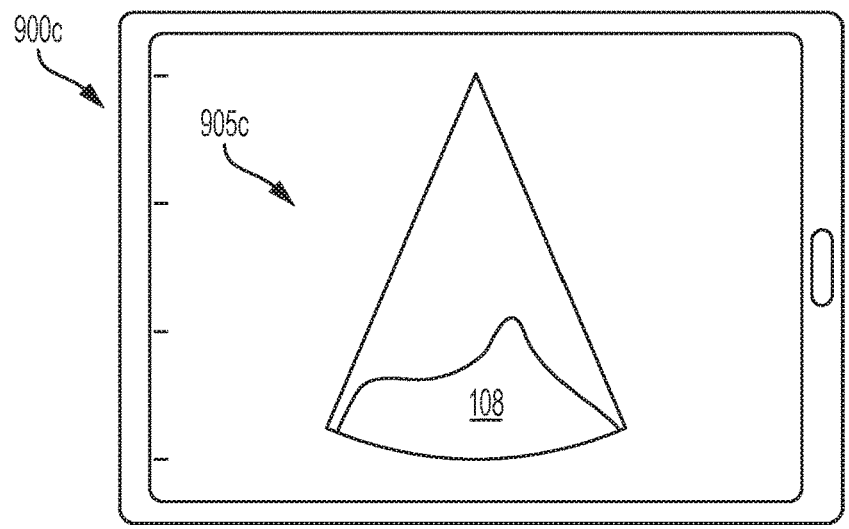

Referring to FIGS. 9A-9C, shown there generally as 900a-900c are a sequence of user interface interactions for receiving input to decrease the sector angle of a sector image during ultrasound imaging, in accordance with at least one embodiment of the present invention. The embodiments shown in FIGS. 9A-9C are similar to the embodiments of FIGS. 8A-8C, except they show the corresponding input for decreasing the sector angle of a sector image instead of increasing the sector angle. FIGS. 9A-9C illustrate an embodiment of the performance of the method of FIG. 2; and the discussion below will again be made with reference to the acts of FIG. 2.

Referring to FIG. 9A, shown there generally as 900a is the display of a live ultrasound image feed 905a showing structure 108 (act 205 in FIG. 2), in accordance with an embodiment of the present invention. An ultrasound operator may wish to decrease the sector angle of the sector image being displayed. In the present embodiments, the touchscreen may be configured to receive a pinch gesture input for decreasing the sector angle. As illustrated, the two touch points for the pinch gesture may be initiated at touchpoints 912a. The beginning of this touch input may constitute act 210 in FIG. 2. As illustrated in FIG. 9A, the sector image may have a wide sector angle that shows multiple structures 108, 850, 852.

Referring to FIG. 9B, shown there generally as 900b is an example transitional view of the ultrasound image feed 905a shown in FIG. 9A, in accordance with an embodiment of the present invention. For example, FIG. 9B illustrates an example user interface interaction at a point in time after contact with the touchscreen is initiated in FIG. 9A. As illustrated, a pinch-in gesture is initiated from touchpoints 912a in FIG. 9A and extended to touchpoints 912b in FIG. 9B; and continuous contact with the touchscreen may be maintained through the touch paths 916 (shown in dotted outline). In response, the touchscreen may display a transitional view during the continuous contact that provides previews 920 of the desired sector angle for the sector image (act 215 in FIG. 2).

Referring still to FIG. 9B, the illustrated example embodiment may update the appearance of the ultrasound image feed to show previews 920 of the sector angle that corresponds to characteristics of the touch on the touchscreen (act 220 in FIG. 2). For example, in some embodiments, the transitional view may be continuously updated to correspond to characteristics of the contact with the touchscreen. As illustrated, this may include the previews 920 of the live ultrasound image feed 905a being continuously updated to provide a view of how an ultrasound image feed with a projected narrower sector angle will appear. This may result in the portion of the ultrasound image feed 905a that remains viewable decreasing with the length of the pinch-in gesture.

As noted above, when generating the transitional view encompassing the previews 920, scan conversion may be repeatedly performed on the image data from the ultrasound signals to configure the image data to be displayed by the previews 920. In some embodiments, such scan conversion may include reading only the portion of the image data of the original ultrasound image feed 905a that corresponds to the narrower sector angle indicated by the pinch-in gesture. For example, in the illustrated previews 920 of FIG. 9B, a narrower view of the original ultrasound image feed 905a is displayed and only structure 108 is viewable. However, structures 850, 852 formerly viewable in the ultrasound image feed 905a shown in FIG. 9A are not viewable in the previews 920 of FIG. 9B. In some embodiments, the previews 920 may also provide an indication of the sector angle of the original ultrasound image feed 905a from which the sector angle is being decreased. As illustrated in FIG. 9B, this is shown in dotted outline.

In some embodiments, the live ultrasound image feed originally appearing prior to the beginning of the contact with the touchscreen (e.g., image feed 905a from FIG. 9A in the illustrated examples) may continue to be displayed. For example, as the previews 920 showing how an ultrasound image feed with a narrower sector angle may appear are being displayed, data from the live ultrasound image feed 905a that remains viewable may continue to be displayed. For example, if there is motion in the structure 108, the previews 920 viewable during the continuous contact with the touchscreen may continue to show this motion as the previews 920 are being generated and displayed in FIG. 9B.

Referring still to FIG. 9B, the previews 920 of the ultrasound image feed 905a may continue to be updated while there is continuous contact with the touchscreen (the 'NO' branch at act 225 in FIG. 2). However, upon termination of the continuous contact with the touchscreen (the 'YES' branch at act 225 in FIG. 2), a setting for the sector angle imaging parameter may be selected based on the preview being displayed (act 230 in FIG. 2). For example, in the context of the example scenario of FIG. 9B, the sector angle of the ultrasound image feed 905a that remains viewable, as indicated by the preview 920 being displayed, may be selected to be the desired sector angle.

Referring to FIG. 9C, shown there generally as 900c is an example view of the ultrasound image feed that has been updated after the sector angle imaging parameter has been selected, in accordance with an embodiment of the present invention. To confirm the selection of the sector angle, the selected parameters for the sector angle shown in the previews 920 of FIG. 9B (as may be identified by the remaining portion of the original ultrasound image feed 905a that remains viewable) may be used to alter the ultrasound sequence of the transducer array in the ultrasound acquisition unit. This may allow contraction of the range of angles for the ultrasound signals being emitted and received by the ultrasound transducer. As can be seen, the ultrasound image feed 905c of FIG. 9C shows an updated ultrasound image feed that has a narrower sector angle. In this narrower-angle sector image, the structure 108 is viewable. However, the additional structures 850, 852 previously viewable in the wider-angle sector image of FIG. 9A are no longer viewable. Upon completion of the updating of the sector angle image parameter to a narrower sector angle, the ultrasound signals being emitted and received from the ultrasound transducer may be focused in a narrower range of angles, so that each sweep of the ultrasound signals may either be performed more quickly (and thereby allow increased frame rate) and/or be performed with additional signals focused in the narrower angle range (so as to allow for increased lateral resolution).

The embodiments described in FIGS. 8A-8C and 9A-9C provide a mechanism to alter sector angle without the repeated trial and error required by activation of manual or touchscreen button presses. This may enhance operator efficiency when they modify the sector angle. Additionally, since the repeated button presses typically result in repeated updating of the ultrasound sequence that cause the screen to flicker or jump when the image data is re-acquired, the present embodiments may allow for a smooth transition to preview the desired sector angle without such screen flickers and jumps.

Figure 10:
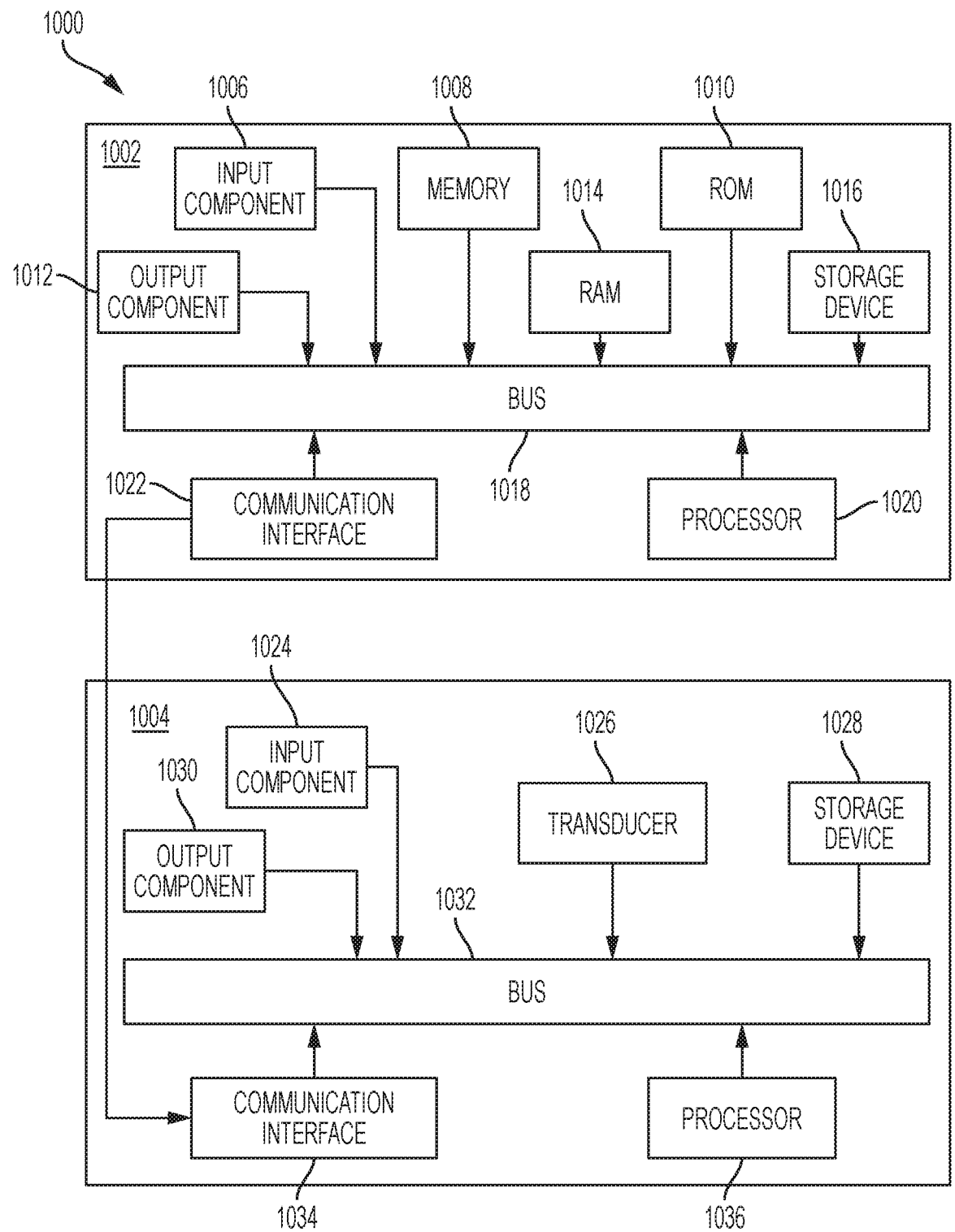
FIG. 10 shows a functional block diagram of an ultrasound system, in accordance with at least one embodiment of the present invention.

Referring to FIG. 10, shown there generally as 1000 is a functional block diagram of an ultrasound system, in accordance with at least one embodiment of the present invention. For example, the ultrasound imaging system 1000 may be configured to perform the method of FIG. 2, and provide the various user interfaces shown in FIGS. 3A-9C.

Ultrasound imaging system 1000 may include an ultrasound acquisition unit 1004 configured to transmit ultrasound energy to a target object, receive ultrasound energy reflected from the target object, and generate ultrasound image data based on the reflected ultrasound energy. The ultrasound acquisition unit 1004 may include a transducer 1026 which converts electric current into ultrasound energy and vice versa. Transducer 1026 may transmit ultrasound energy to the target object which echoes off the tissue. The echoes may be detected by a sensor in transducer 1026 and relayed through a bus 1032 to a processor 1036. Processor 1036 may interpret and process the echoes to generate image data of the scanned tissue. In some embodiments, the ultrasound acquisition unit 1004 (or various components thereof) may be provided as a handheld ultrasound probe that is in communication with other components of the ultrasound imaging system 1000. For example, the handheld probe may include the transducer 1026 of ultrasound acquisition unit 1004. Ultrasound acquisition unit 1004 may also include storage device 1028 (coupled to and accessible by bus 1032) for storing software or firmware instructions, configuration settings (e.g., sequence tables), and/or ultrasound image data.

Although not illustrated, as will be apparent to one of skill in the art, the ultrasound imaging system 1000 may include other components for acquiring, processing and/or displaying ultrasound image data. These include, but are not limited to: a scan generator, transmit beamformer, pulse generator, amplifier, analogue to digital converter (ADC), receive beamformer, signal processor, data compressor, wireless transceiver and image processor. Each of these may be components of ultrasound acquisition unit 1004 and/or electronic display unit 1002 (described below).

Ultrasound imaging system 1000 may include an electronic display unit 1002 which is in communication with ultrasound acquisition unit 1004 via communication interfaces 1022/1034. In various embodiments, communication interfaces 1022/1034 may allow for wired or wireless connectivity (e.g., via Wi-Fi™ and/or Bluetooth™) between the electronic display unit 1002 and the ultrasound acquisition unit 1004. Electronic display unit 1002 may work in conjunction with ultrasound acquisition unit 1004 to control the operation of ultrasound acquisition unit 1004 and display the images acquired by the ultrasound acquisition unit 1004. An ultrasound operator may interact with the user interface provided by display unit 1002 to send control commands to the ultrasound acquisition unit 1004 to adjust various imaging parameters such as depth, zoom, etc. The electronic display unit 1002 may be a portable device, which may include a mobile device (e.g. smartphone), tablet, laptop, or other suitable device incorporating a display and a processor and capable of accepting input from a user and processing and relaying the input to control the operation of the ultrasound acquisition unit 1004 as described herein.

Each of ultrasound acquisition unit 1004 and display unit 1002 may have one or more input components 1024, 1006 and/or one or more output components 1030, 1012. In the FIG. 10 embodiment, ultrasound acquisition unit 1004 may include an input component 1024 which is configured to accept input from the user (e.g., to turn on the ultrasound acquisition unit 1004 or control the connection of the ultrasound acquisition unit to the electronic display unit 1002). For example, in some embodiments, ultrasound acquisition unit 1004 may also include an output component 1030, such as a LED indicator light which can output the status of the ultrasound acquisition unit 1004.

In the FIG. 10 embodiment, display unit 1002 may include an input component 1006 configured to accept input from the user. Certain input received at input component 1006 may be relayed to ultrasound acquisition unit 1004 to control the operation of ultrasound acquisition unit 1004. Display unit 1002 may also include an output component 1012, such as a display screen, which displays images based on image data acquired by ultrasound acquisition unit 1004. In particular embodiments, display unit 1002's input component 1006 may include a touch interface layered on top of the display screen of the output component 1012. Electronic display unit 1002 may also include memory 1008, Random Access Memory (RAM) 1014, Read Only Memory (ROM) 1010, and persistent storage device 1016, which may all be connected to bus 1018 to allow for communication therebetween and with processor 1020. Any number of these memory elements may store software or firmware that may be accessed and executed by processor 1020 to perform the methods and provide the user interfaces described herein.

In some embodiments, all of the input controls and display screen necessary for the operation of the ultrasound imaging system 1000 may be provided by input and output components 1006, 1012 of the display unit 1002. In such cases input and output components 1024, 1030 of ultrasound acquisition unit 1004 may be optional and/or omitted. In certain embodiments, the ultrasound acquisition unit 1004 may be a handheld probe (i.e. including transducer 1026) which is in communication with the display unit 1002 over the communications interfaces 1022/1034 to facilitate operation of the ultrasound acquisition unit 1004 and processing and display of ultrasound images.

In various embodiments, at least a portion of the processing of the image data corresponding to the reflected ultrasound energy detected by the handheld probe's transducer 1026 may be performed by one or more of processors internal to the ultrasound acquisition unit 1004 (such as by the processor 1036) and/or by processors external to the ultrasound acquisition unit 1004 (such as the processor 1020 of electronic display unit 1002). By having some of the image data processing tasks typically performed by a processor 1036 of ultrasound acquisition unit 1004 be performed instead by a processor 1020 of the display unit 1002, less physical processing hardware may need to be provided on the ultrasound acquisition unit 1004. This may facilitate a lightweight, portable design and construction for the ultrasound acquisition unit 1004 (e.g., when it is a handheld probe). In particular embodiments the handheld probe may have a mass that is less than approximately 1 kg (2 lbs).

In some embodiments, the output component 1030 of ultrasound acquisition unit 1004 may include a display screen, which can be configured to display or otherwise output the images acquired by ultrasound acquisition unit 1004 (in addition to or alternative to displaying such images on the display unit 1002).

As noted, the ultrasound imaging system 1000 of FIG. 10 may be configured to perform the method of FIG. 2, so as to receive the touch input and display the sequences of user interfaces discussed above. The discussion below will be made with simultaneous reference to FIG. 2 and the components of FIG. 10, to illustrate how such components may be involved in performing various acts of the method of FIG. 2. Steps of method 200 in FIG. 2 may be implemented as software or firmware contained in a program memory 1008, 1014, 1010 or storage device 1016 accessible to a processor 1020 of display unit 1002 of FIG. 10. Processor 1020 may implement method 200 of FIG. 2 by executing software instructions provided by the software.

For example, when doing so, the initial imaging parameters shown in the live ultrasound image feed may be defined by the current or initial imaging parameters of ultrasound acquisition unit 1004 and/or electronic display unit 1002. Where no adjustments have yet been made to the imaging parameters, the current or initial imaging parameters may include the initial imaging parameters that have been set by the user (automatically based on the user's preferences or manually) or that have been pre-loaded to the electronic display unit 1002 (e.g. from manufacturer's settings).

Ultrasound image data may be obtained, for example, by ultrasound acquisition unit 1004 employing a high frequency, high voltage pulse to excite transducer 1026 to emit ultrasound waves and receiving the reflected ultrasound waves. In particular embodiments, the ultrasound acquisition unit 1004 may be a probe which acquires ultrasound image data by generating pulses of a specified amplitude in accordance with an ultrasound sequence specified in a sequence table. The probe may perform ultrasound beam generation using transmit beamforming, detects and receives the ultrasound echo and performs receive beamforming, and processes the data based on the sequence specified in the sequence table. The probe may transmit the processed ultrasound image data to a display unit 1002 which has a processor 1020 that further processes the data for display (e.g. scan conversion) and then displays the ultrasound image on the output component (e.g., screen) 1012.

Scan conversion may then be performed on the data to transform the image data in a manner that allows it to be displayed in a form that is more suitable for human visual consumption. For example, this may involve converting the image data from the data space (e.g. polar coordinate form) to the display space (e.g. Cartesian coordinate form). The acquired ultrasound images may be displayed on the output component 1012 of display unit 1002 (act 205 of FIG. 2). Scan conversion is one of the actions that renders the image data suitable for display. However, as will be apparent to those of skill in the art, other technological steps may also need to be performed, such as, for example, amplification and/or digitization of the data. After the scan conversion, an ultrasound image may be displayed by the electronic display unit 1002.

If an ultrasound operator wishes to modify the imaging parameters, they may input a touchscreen command to direct the ultrasound imaging system 100 via the touchscreen of the electronic display unit 1002 (act 210 of FIG. 2). For example, the input component 1006 of display unit 1002 may include a touch interface that detects the user input and interprets the command based on the user input being received. The touchscreen interface may receive the input and provide it to processor 1020 which executes software instructions to analyse the input and determine the command associated with the input.

During continuous contact with the touchscreen, transitional views of the live ultrasound image feed with previews of the image parameters adjusted may be displayed at the electronic display unit 1002 (act 215 of FIG. 2). As the continuous contact with the touchscreen proceeds, the previews may be updated in accordance with characteristics of the touchscreen contact (act 220 of FIG. 2). In some embodiments, the acquisition and display of the ultrasound images are frozen or paused while the previews are being generated and displayed. In other embodiments, the previews can be generated and displayed while continuing to display the live ultrasound image feed (e.g., in real time). In such embodiments, the previews may be based on live ultrasound image data being acquired using the existing ultrasound sequence that the processor 1036 was configuring the transducer 1026 to transmit and receive ultrasound signals with prior to the receipt of touch input.

A determination may then be made as to whether contact with the touchscreen has been terminated (act 225 of FIG. 2). If so, a selected setting of the imaging parameter may be identified based on the preview being displayed when the contact with the touchscreen is terminated (act 230 of FIG. 2). Although the various embodiments discussed above have generally been with respect to identifying a selected setting upon termination of touch with the touchscreen, this may not be necessary in all embodiments. For example, in some embodiments, instead of awaiting termination of contact with the touchscreen to identify a selected setting, a selected setting may be identified when a pause or stop in the gesture is detected for at least a period of time (but without contact with the touchscreen being terminated). This identified setting may then be transmitted via communication interfaces 1022/1034 to the ultrasound acquisition unit 1004. In some embodiments, the identified setting may be used to update the ultrasound sequence being used by the transducer 1026 to transmit and receive ultrasound signals. In cases where the live ultrasound image feed was paused during the transitional view and generation of previews, the live ultrasound image feed may be resumed.

In various embodiments, the same touch gesture may serve to be input for modifying different types of imaging parameters, depending on the context. For example, where the displayed image is not in a zoomed in state, then, as discussed above, a drag gesture having a vertical component may be interpreted as a command to increase or decrease the imaging depth. However, where the displayed image is in a zoomed-in state (e.g., the user has used a pinch-out gesture to perform a write zoom on a ROI), then a drag gesture may be interpreted as a command to pan the image in the direction of the drag gesture (and update the ROI accordingly), as opposed to a command to adjust the imaging depth. Accordingly, in some embodiments, the display unit 1002 may interpret a drag gesture to adjust either the pan or imaging depth based on the zoom state of the displayed image.

In some embodiments, where the input is in tactile form with the touchscreen, the input component 1006 of display unit 1002 may be configured to be operated with one hand and/or is handheld, so that the user is free to use his or her other hand to hold and operate the ultrasound acquisition unit 1004 (e.g. such as a handheld probe).

As noted, the input may include sustained (e.g., continuous) contact by one or more of the fingers of a user of the display unit 1002. Two example touch gestures (drag and pinch) have been discussed above for altering various imaging parameters. However, in some embodiments, the input may include additional or alternative types of touch input (e.g., touch gestures with more than two fingers, swipe gestures in from beyond the edge of the screen, pressure-sensitive touches, and the like). For example, touch commands which may be recognized include: a quick downward or upward swipe (or other touch gesture) indicating that the image is to be flipped vertically (e.g., along a horizontal axis); a quick sideways or lateral swipe (or other touch gesture) indicating that the image is to be flipped horizontally (e.g., along a vertical axis); dragging fingers in a circular motion, indicating that the image is to be rotated (e.g., in a clockwise or counter-clockwise direction); dragging the fingers in any direction on the screen to change the section of the image that is displayed in the display screen (panning of the image); and the like.

As will be appreciated upon reading this description, the apparatus, systems and methods described herein may help to alleviate some drawbacks of traditional ultrasounds systems. In some embodiments, the user interface may enable handheld operation and control of the display unit 1002 and ultrasound acquisition unit 1004. For example, many of the controls can be performed with the ultrasound operator's fingers alone, on the same hand that is holding the display unit 1002, leaving the operator's other hand free to hold and operate the ultrasound acquisition unit 1004 (e.g. the ultrasound probe). The embodiments described herein may reduce the number of separate user controls (either on-screen or off-screen) required to operate the ultrasound acquisition unit 1004 and display unit 1002. The present embodiments may also simplify the user experience, and remove the ambiguities of the button controls noted above. In addition, incorporation of multi-touch, pinch-zoom gestures on the touchscreen interface may allow for more versatile and/or granular control of a ROI on the display unit 1002.

Moreover, for some applications, it is desirable to maintain the skin line in the ultrasound image (unless the user wishes to zoom in on a particular area). It can be difficult to maintain the skin line if the user has to break eye contact with the display screen in order to operate physical controls (as is required for conventional ultrasound acquisition systems) or is required to focus on another part of the screen (as is required for touchscreen interfaces that provide on-screen buttons). However, the embodiments described herein may help to avoid this drawback since the user can maintain eye contact with the live ultrasound image feed while the transitional view and associated previews are being display for an image parameter being adjusted.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

Interpretation of Terms

Unless the context clearly requires otherwise, throughout the description and the "comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally include "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are:

one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, mobile computers, mobile devices, tablet computers, desktop computers, server computers, cloud computers, mainframe computers, computer workstations, and the like. For example, one or more data processors in a control circuit for a device may implement methods as described herein by executing software instructions in a program memory accessible to the processors. In another example, a tablet computer or other portable computing device having a touchscreen may implement methods as described herein by having processors provided therein execute software instruction in a program memory accessible to such processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may include any non-transitory medium which carries a set of computer-readable instructions which, when executed by a data processor (e.g., in a controller, ultrasound processor in an ultrasound machine, and/or a processor in an electronic display unit), cause the data processor to execute a method of the present embodiments. Program products may be in any of a wide variety of forms. The program product may include, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method of controlling visualization of ultrasound image data, comprising:
    displaying a live 2-D ultrasound image feed on a touchscreen, the live 2-D ultrasound image feed being acquired by an ultrasound acquisition unit with a physical orientation cue;
    while displaying the live 2-D ultrasound image feed on the touchscreen, displaying a visual orientation indicator that corresponds to the physical orientation cue on the ultrasound acquisition unit;
    receiving input via the touchscreen to flip the live 2-D ultrasound image feed along one of a vertical axis or a horizontal axis, the input comprising continuous contact with the touchscreen;
    during the continuous contact with the touchscreen, displaying a transitional view of the live 2D ultrasound image feed that is continuously updated in accordance with characteristics of the contact with the touchscreen;
    upon termination of the continuous contact with the touchscreen, determining whether a pre-flipped orientation of the live 2-D ultrasound image feed or a flipped orientation of the live 2-D ultrasound image feed will be displayed, the determining being based on a position on the touchscreen where the continuous contact with the touchscreen is terminated, wherein the live 2-D ultrasound image feed comprises equivalent content in both the pre-flipped orientation and the flipped orientation; and
    based on the determining, displaying the live 2-D ultrasound image feed in the pre-flipped orientation or the flipped orientation.

2. The method of claim 1, wherein the continuous contact with the touchscreen corresponds to a drag gesture, and the transitional view of the live 2D ultrasound image feed comprises an animation from the pre-flipped orientation of the live 2-D ultrasound image feed to the flipped orientation of the live 2-D ultrasound image feed.

3. The method of claim 2, when displaying the transitional view of the live 2D ultrasound image feed that is continuously updated in accordance with the characteristics of the contact with the touchscreen, scan conversion is repeatedly performed to adapt image data from being displayed in the pre-flipped orientation to being displayed in a partially-flipped orientation within the animation.

4. The method of claim 2, wherein the transitional view of the live 2D ultrasound image feed being continuously updated in accordance with the characteristics of the contact with the touchscreen comprises the animation being continuously updated to correspond with a length of the drag gesture.

5. The method of claim 2, wherein the received input via the touchscreen to flip the live 2-D ultrasound image feed comprises selecting the visual orientation indicator to initiate the drag gesture, and the animation from the pre-flipped orientation of the live 2-D ultrasound image feed to the flipped orientation of the live 2-D ultrasound image feed comprises rotating the live 2-D ultrasound image feed, wherein a degree of the rotation corresponds to a distance the visual orientation indicator is from a center of a display of the touchscreen during the drag gesture.

6. The method of claim 5, wherein the position on the touchscreen where the drag gesture is terminated is past the center of the display, and based on the position, the flipped orientation of the live 2-D ultrasound image feed is determined to be displayed.

7. The method of claim 6, wherein upon termination of the drag gesture, the animation from the pre-flipped orientation of the live 2-D ultrasound image feed to the flipped orientation of the live 2-D ultrasound imaged feed is partially rotated, and the method further comprises displaying a completion of the animation to the flipped orientation of the live 2-D ultrasound image feed prior to displaying the live 2-D ultrasound image feed in the flipped orientation.

8. The method of claim 5, wherein the position on the touchscreen where the drag gesture is terminated is not past the center of the display, and the pre-flipped orientation of the live 2-D ultrasound image feed is determined to be displayed.

9. The method of claim 8, wherein upon termination of the drag gesture, the animation from the pre-flipped orientation of the live 2-D ultrasound image feed to the flipped orientation of the live 2-D ultrasound imaged feed is partially rotated, and the method further comprises displaying a reversion of the animation to the pre-flipped orientation of the live 2-D ultrasound image feed prior to displaying the live 2-D ultrasound image feed in the pre-flipped orientation.

10. The method of claim 1, wherein when displaying the transitional view of the live 2D ultrasound image feed that is continuously updated in accordance with the characteristics of the contact with the touchscreen, image data continues to be acquired and displayed in the live 2-D ultrasound image feed.

11. The method of claim 1, wherein the ultrasound acquisition unit is usable in multiple types of exams comprising non-cardiac exams and cardiac exams, and the received input via the touchscreen is for flipping the live 2-D ultrasound image feed along the vertical axis.

12. The method of claim 1, wherein the ultrasound acquisition unit is usable for multiple types of exams comprising urological exams, and the received input via the touchscreen is for flipping the live 2-D ultrasound image feed along the horizontal axis.

13. An ultrasound imaging system comprising:
an ultrasound acquisition unit configured to transmit and receive ultrasound signals, the ultrasound acquisition unit having a physical orientation cue; and
a display computing device comprising a processor, a memory storing instructions for execution by the processor, and a touchscreen, the display computing device being communicably coupled to the ultrasound acquisition unit, wherein when the instructions are executed by the processor, the processor is configured to:
display a live 2-D ultrasound image feed on the touchscreen, the live 2-D ultrasound image feed being acquired by the ultrasound acquisition unit;
while displaying the live 2-D ultrasound image feed on the touchscreen, display a visual orientation indicator that corresponds to the physical orientation cue on the ultrasound acquisition unit;
receive input via the touchscreen to flip the live 2-D ultrasound image feed along one of a vertical axis or a horizontal axis, the input comprising continuous contact with the touchscreen;
during the continuous contact with the touchscreen, display a transitional view of the live 2D ultrasound image feed that is continuously updated in accordance with characteristics of the contact with the touchscreen;
upon termination of the continuous contact with the touchscreen, determine whether a pre-flipped orientation of the live 2-D ultrasound image feed or a flipped orientation of the live 2-D ultrasound image feed will be displayed, the determining being based on a position on the touchscreen where the continuous contact with the touchscreen is terminated, wherein the live 2-D ultrasound image feed comprises equivalent content in both the pre-flipped orientation and the flipped orientation; and
based on the determining, display the live 2-D ultrasound image feed in the pre-flipped orientation or the flipped orientation.

14. The ultrasound imaging system of claim 13, wherein the continuous contact with the touchscreen corresponds to a drag gesture, and the transitional view of the live 2D ultrasound image feed comprises an animation from the pre-flipped orientation of the live 2-D ultrasound image feed to the flipped orientation of the live 2-D ultrasound image feed.

15. The ultrasound imaging system of claim 14, wherein the received input via the touchscreen to flip the live 2-D ultrasound image feed comprises selecting the visual orientation indicator to initiate the drag gesture, and the animation from the pre-flipped orientation of the live 2-D ultrasound image feed to the flipped orientation of the live 2-D ultrasound image feed comprises rotating the live ultrasound image feed, wherein a degree of the rotation corresponds to a distance the visual orientation indicator is from a center of the display during the drag gesture.

16. The ultrasound imaging system of claim 15, wherein the position on the touchscreen where the drag gesture is terminated is past the center of the display, and based on the position, the flipped orientation of the live 2-D ultrasound image feed is determined to be displayed.

17. The ultrasound imaging system of claim 16, wherein upon termination of the drag gesture, the animation from the pre-flipped orientation of the live 2-D ultrasound image feed to the flipped orientation of the live 2-D ultrasound imaged feed is partially rotated, and wherein the processor is further configured to display a completion of the animation to the flipped orientation of the live 2-D ultrasound image feed prior to displaying the live 2-D ultrasound image feed in the flipped orientation.

18. The ultrasound imaging system of claim 15, wherein the position on the touchscreen where the drag gesture is terminated is not past the center of the display, and the pre-flipped orientation of the live 2-D ultrasound image feed is determined to be displayed.

19. The ultrasound imaging system of claim 18, wherein upon termination of the drag gesture, the animation from the pre-flipped orientation of the live 2-D ultrasound image feed to the flipped orientation of the live 2-D ultrasound imaged feed is partially rotated, and the system enables the display of a reversion of the animation to the pre-flipped orientation of the live 2-D ultrasound image feed prior to displaying the live 2-D ultrasound image feed in the pre-flipped orientation.

20. A non-transitory computer readable medium storing instructions for execution by a processor of a display computing device having a touchscreen, wherein when the instructions are executed by the processor, the processor is configured to:

display a live 2-D ultrasound image feed on the touchscreen, the live 2-D ultrasound image feed being acquired by an ultrasound acquisition unit with a physical orientation cue;

while displaying the live 2-D ultrasound image feed on the touchscreen, display a visual orientation indicator that corresponds to the physical orientation cue on the ultrasound acquisition unit;

receiving input via the touchscreen to flip the live 2-D ultrasound image feed along one of a vertical axis or a horizontal axis, the input comprising continuous contact with the touchscreen;

during the continuous contact with the touchscreen, display a transitional view of the live 2D ultrasound image feed that is continuously updated in accordance with characteristics of the contact with the touchscreen;

upon termination of the continuous contact with the touchscreen, determine whether a pre-flipped orientation of the live 2-D ultrasound image feed or a flipped orientation of the live 2-D ultrasound image feed will be displayed, the determining being based on a position on the touchscreen where the continuous contact with the touchscreen is terminated, wherein the live 2-D ultrasound image feed comprises equivalent content in both the pre-flipped orientation and the flipped orientation; and based on the determining, display the live 2-D ultrasound image feed in the pre-flipped orientation or the flipped orientation.

* * * * *